United States Patent [19]

Chrisman et al.

[11] Patent Number: 5,762,255
[45] Date of Patent: Jun. 9, 1998

[54] SURGICAL INSTRUMENT WITH IMPROVEMENT SAFETY LOCKOUT MECHANISMS

[75] Inventors: Lars R. Chrisman, Plano, Tex.; Scott H. Heneveld; Stephen F. Peters, both of Hickory Corners, Mich.

[73] Assignee: Richard-Allan Medical Industries, Inc., Richland, Mich.

[21] Appl. No.: 604,106

[22] Filed: Feb. 20, 1996

[51] Int. Cl.[6] ................................................. A61B 17/068
[52] U.S. Cl. ...................... 227/175.2; 227/19; 227/176.1
[58] Field of Search ............................ 227/175.1, 175.2, 227/175.3, 175.4, 176.1, 178.1, 19

[56] References Cited

U.S. PATENT DOCUMENTS

| | | | |
|---|---|---|---|
| 3,269,630 | 8/1966 | Fleischer | 227/107 |
| 3,275,211 | 9/1966 | Hirsch et al. | 227/124 |
| 3,692,224 | 9/1972 | Astafiev et al. | 227/19 |
| 4,296,881 | 10/1981 | Lee | 227/30 |
| 4,304,236 | 12/1981 | Conta et al. | 128/325 |
| 4,354,628 | 10/1982 | Green | 227/19 |
| 4,383,634 | 5/1983 | Green | 227/19 |
| 4,442,964 | 4/1984 | Becht | 227/8 |
| 4,527,724 | 7/1985 | Chow et al. | 227/8 |
| 4,591,086 | 5/1986 | DiGiovanni | 227/8 |
| 4,646,745 | 3/1987 | Noiles | 128/334 |
| 4,892,244 | 1/1990 | Fox et al. | 227/8 |
| 4,955,959 | 9/1990 | Tompkins et al. | 227/178 |
| 5,005,749 | 4/1991 | Aranyi | 227/19 |
| 5,040,715 | 8/1991 | Green et al. | 227/178 |
| 5,065,929 | 11/1991 | Schulze et al. | 227/19 |
| 5,071,052 | 12/1991 | Rodak et al. | 227/178 |
| 5,083,695 | 1/1992 | Foslien et al. | 227/8 |
| 5,129,570 | 7/1992 | Schulze et al. | 227/19 |
| 5,137,198 | 8/1992 | Nobis et al. | 227/19 |
| 5,156,315 | 10/1992 | Green et al. | 227/178 |
| 5,253,793 | 10/1993 | Green et al. | 227/178 |
| 5,307,976 | 5/1994 | Olson et al. | 227/178 |
| 5,312,023 | 5/1994 | Green et al. | 227/175 |
| 5,314,424 | 5/1994 | Nicholas | 606/41 |
| 5,318,221 | 6/1994 | Green et al. | 227/178 |
| 5,361,001 | 11/1994 | Bryan | 227/175 |
| 5,366,133 | 11/1994 | Geiste | 227/175 |
| 5,395,034 | 3/1995 | Allen et al. | 227/178 |

(List continued on next page.)

FOREIGN PATENT DOCUMENTS

| | | | |
|---|---|---|---|
| 0324638A1 | 1/1989 | European Pat. Off. | A61B 17/10 |
| 0489436A1 | 12/1991 | European Pat. Off. | A61B 17/072 |
| 0514139A2 | 5/1992 | European Pat. Off. | A61B 17/072 |
| 0596543A1 | 5/1992 | European Pat. Off. | A61B 17/072 |
| 9537570A2 | 10/1992 | European Pat. Off. | A61B 17/072 |
| 9576038A1 | 6/1993 | European Pat. Off. | A61B 17/072 |
| 0593920A1 | 9/1993 | European Pat. Off. | A61B 17/072 |
| 1237035 | 6/1960 | France . | |
| 2066723A | 11/1980 | United Kingdom | A61B 17/11 |
| PCT/US95/ 00928 | 1/1995 | WIPO | A61B 17/072 |

Primary Examiner—Scott A. Smith
Attorney, Agent, or Firm—Howard & Howard

[57] ABSTRACT

This invention provides surgical instruments having improved lockout mechanisms. The surgical instruments are of the type which have an operating mechanism for repeatedly performing a surgical procedure and a control mechanism for manipulating the instrument between a neutral position and a ready position for performing the surgical procedure. The instruments comprise a passive lockout assembly and an active lockout assembly. The passive lockout assembly includes a key which is operatively connected to the control mechanism. The key immobilizes the operating mechanism unless the instrument is in the ready position. The active lockout assembly includes a plunger operatively connected to a manually operable switch. The plunger immobilizes the operating mechanism unless the switch is operated and reengages the operating mechanism each time the instrument is used. Each time the instrument is used to perform the surgical operation, therefore, the instrument of the instrument must be in the ready position and the active lockout switch must be operated. Otherwise, the operating mechanism of the instrument is immobilized by one or both of the passive and active lockout assemblies.

16 Claims, 21 Drawing Sheets

U.S. PATENT DOCUMENTS

| | | | |
|---|---|---|---|
| 5,397,046 | 3/1995 | Savage et al. | 227/176 |
| 5,412,267 | 5/1995 | Solyntjes et al. | 227/176 |
| 5,415,335 | 5/1995 | Knobell | 227/180 |
| 5,423,471 | 6/1995 | Mastri et al. | 227/181 |
| 5,425,745 | 6/1995 | Green et al. | 606/219 |
| 5,431,675 | 7/1995 | Nicholas et al. | 606/170 |
| 5,445,304 | 8/1995 | Plyley et al. | 227/176 |
| 5,447,265 | 9/1995 | Vidal et al. | 227/176 |
| 5,452,836 | 9/1995 | Huitema et al. | 227/176 |
| 5,458,279 | 10/1995 | Plyley | 227/176 |
| 5,462,215 | 10/1995 | Viola et al. | 227/176 |
| 5,465,895 | 11/1995 | Knodel et al. | 227/176 |
| 5,465,896 | 11/1995 | Allen et al. | 227/176 |
| 5,470,006 | 11/1995 | Rodak | 227/176 |
| 5,470,008 | 11/1995 | Rodak | 227/176 |
| 5,478,003 | 12/1995 | Green et al. | 227/176 |
| 5,580,067 | 12/1996 | Hamblin et al. | 227/175.2 |
| 5,597,107 | 1/1997 | Knodel et al. | 227/175.2 |

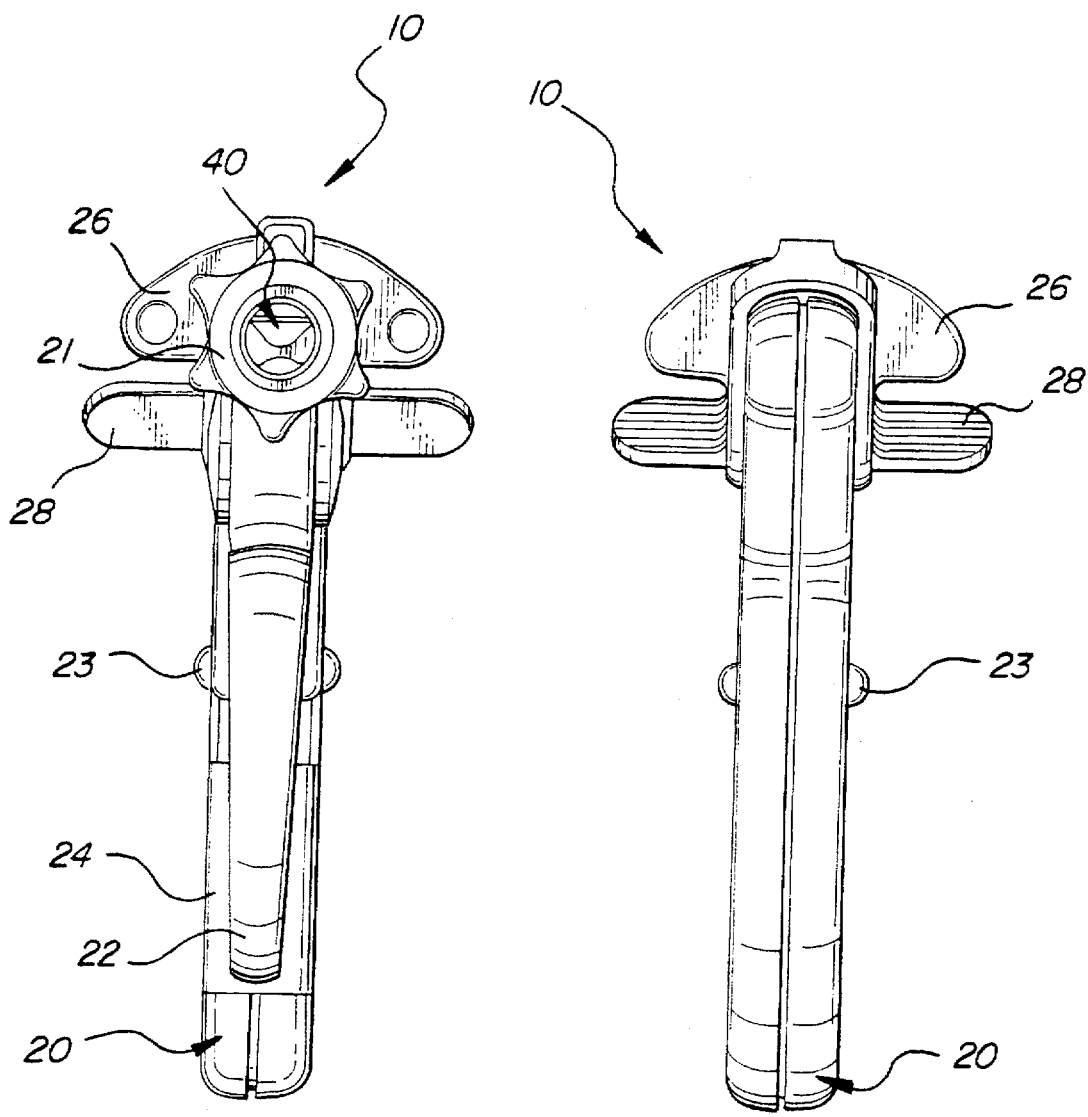

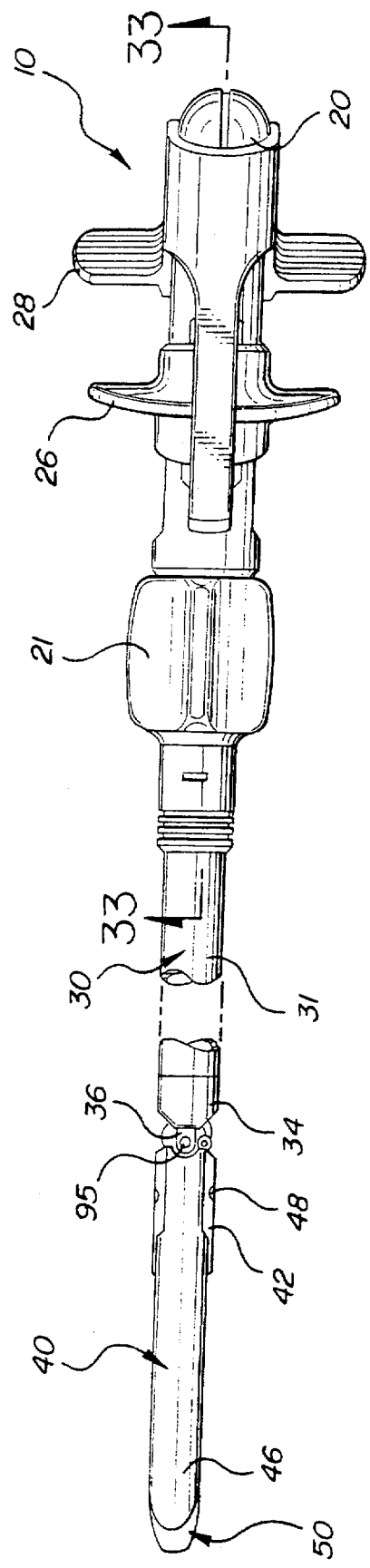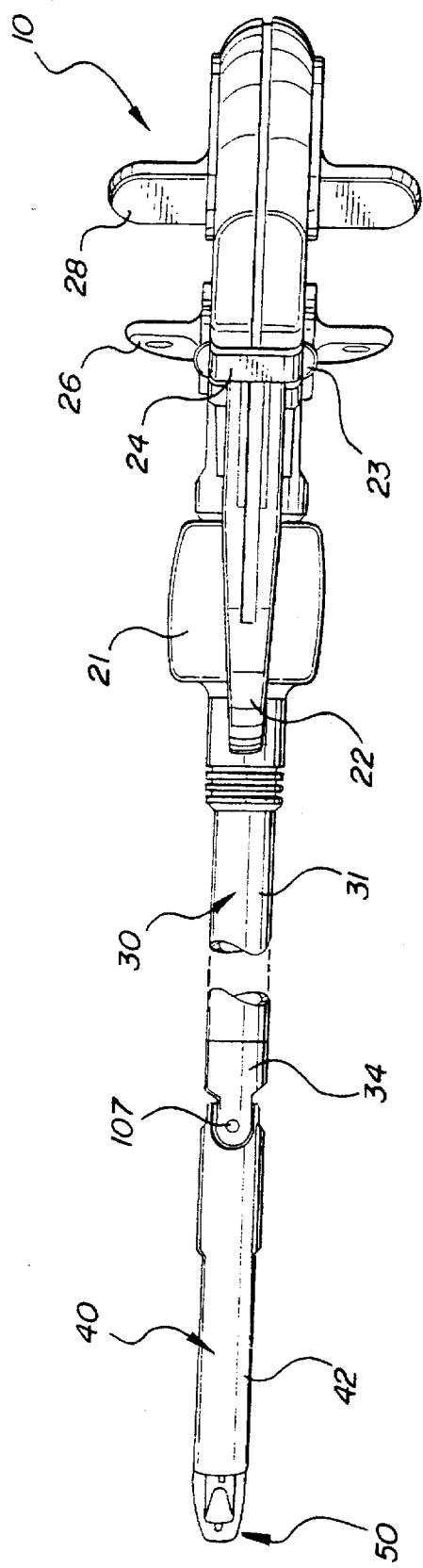

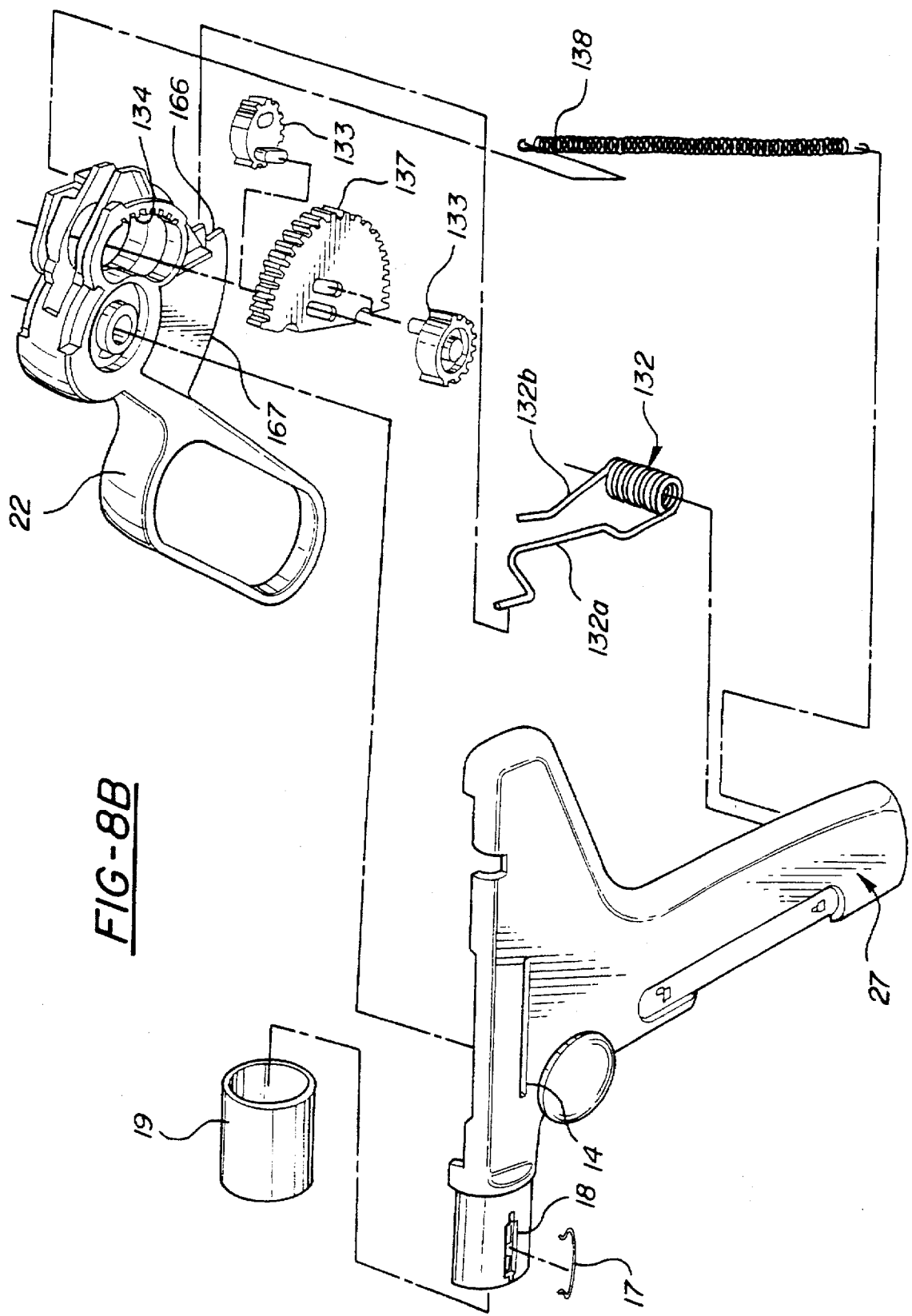

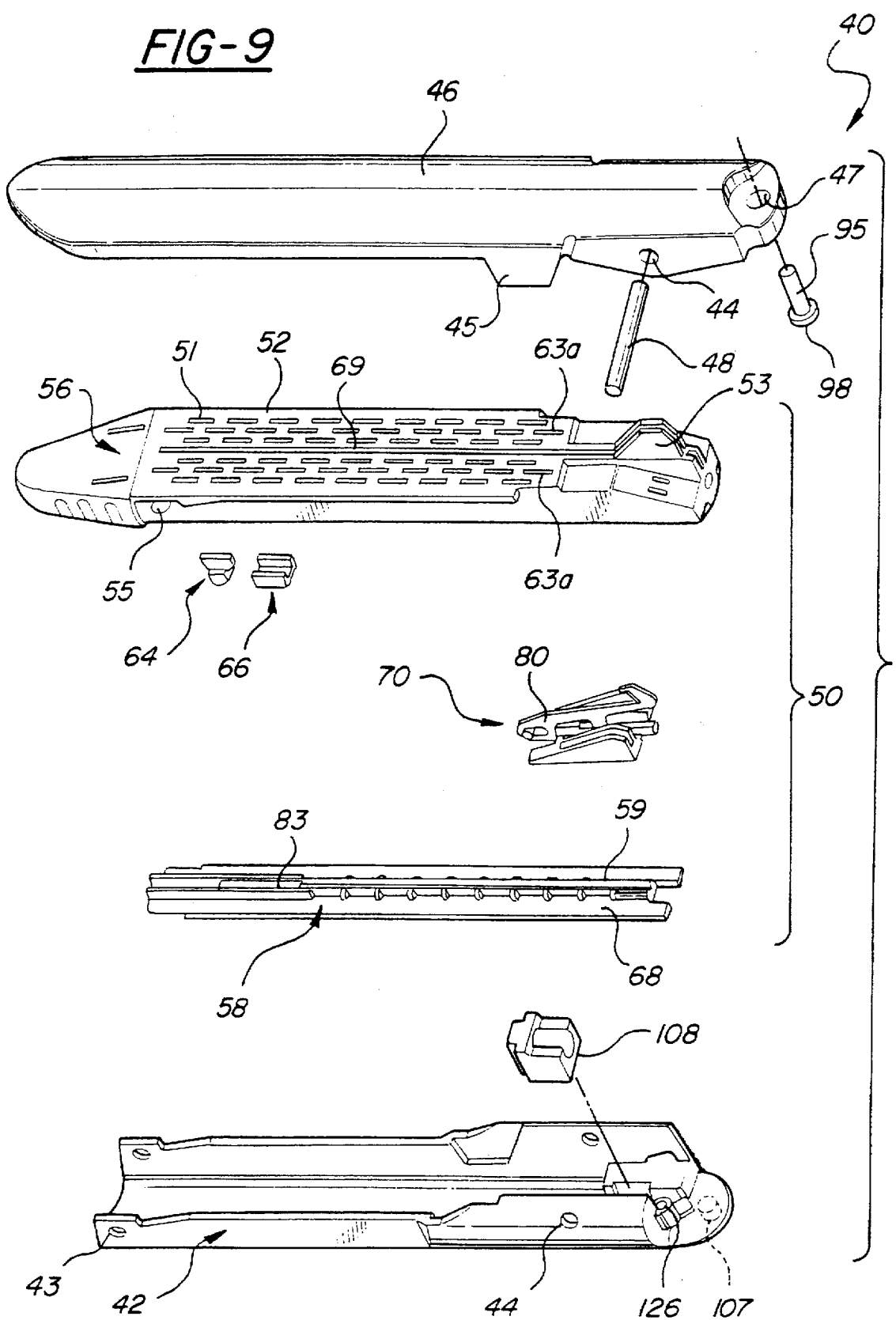

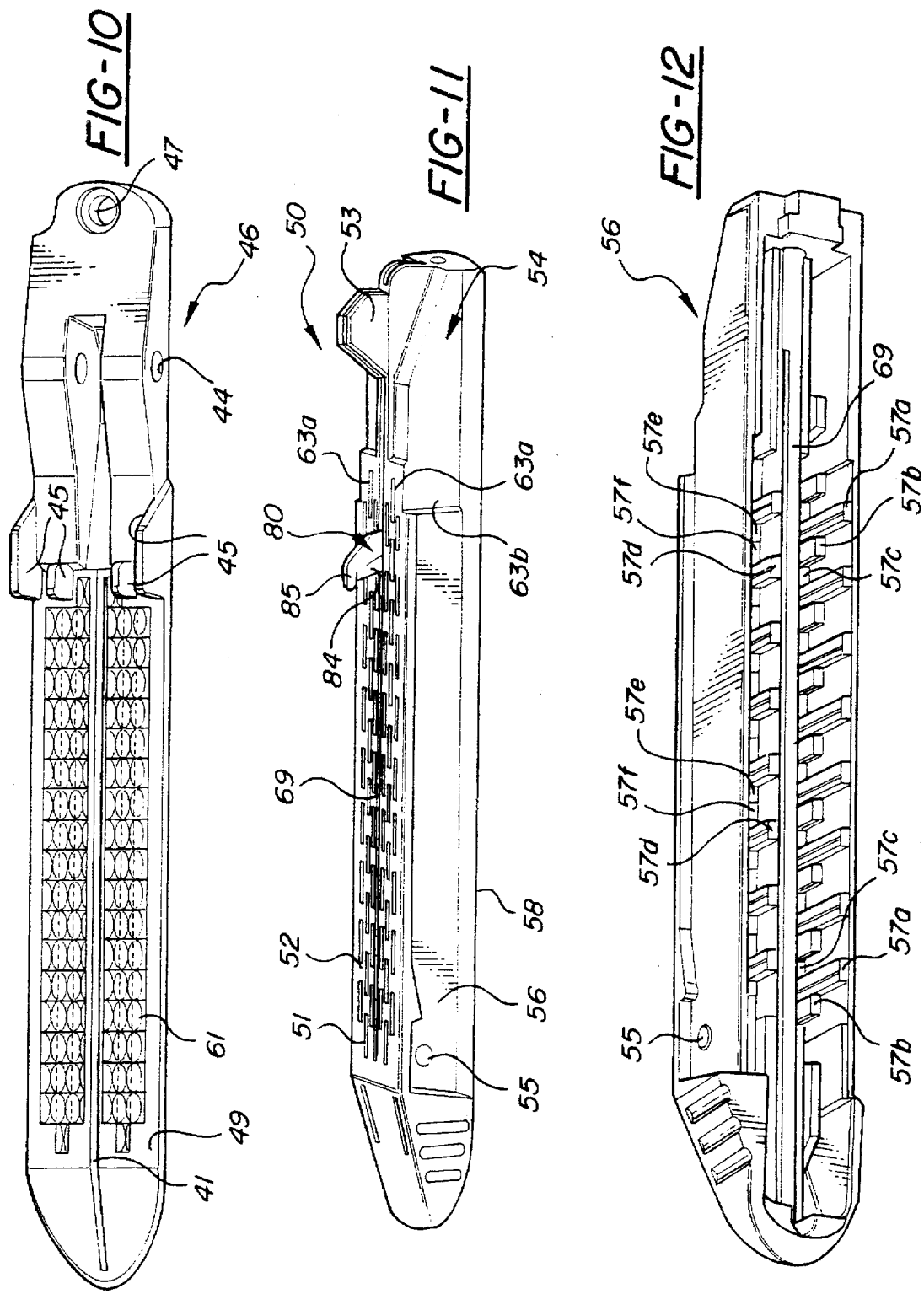

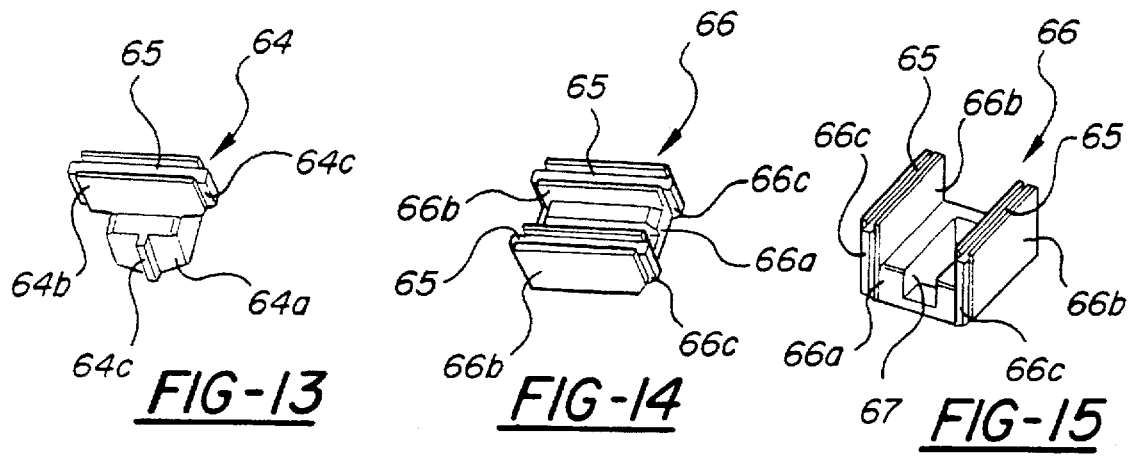
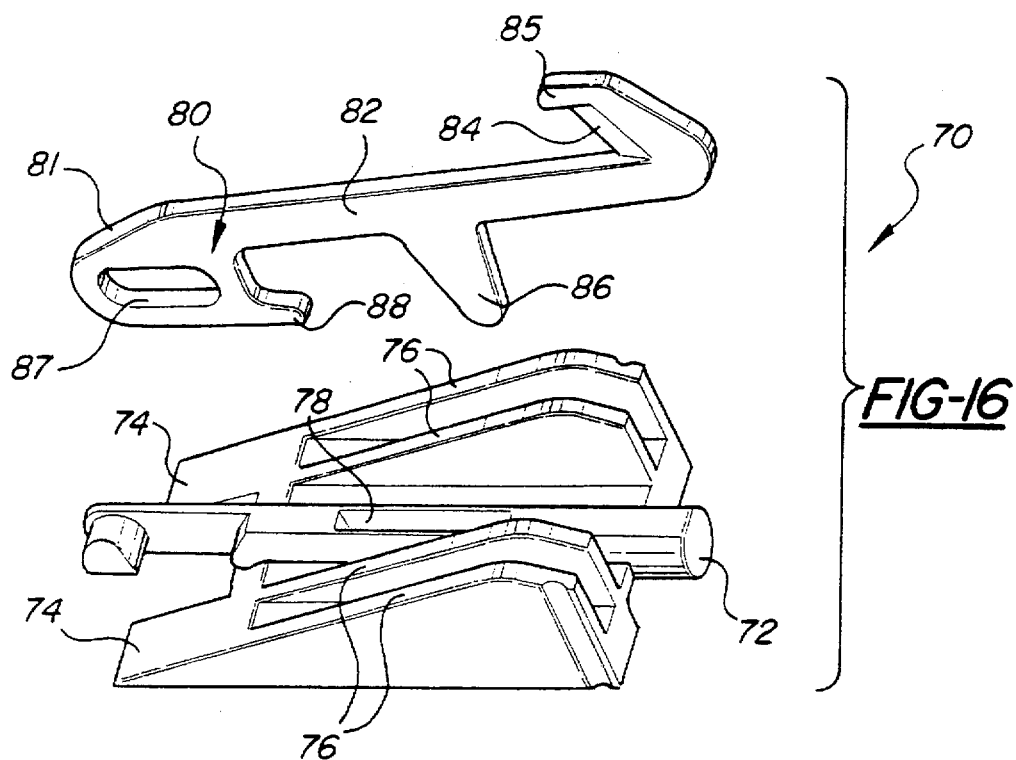
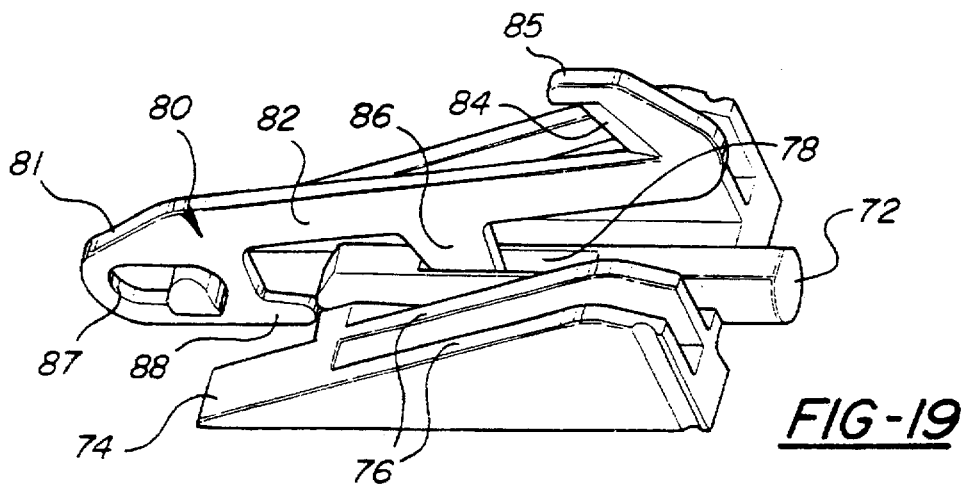

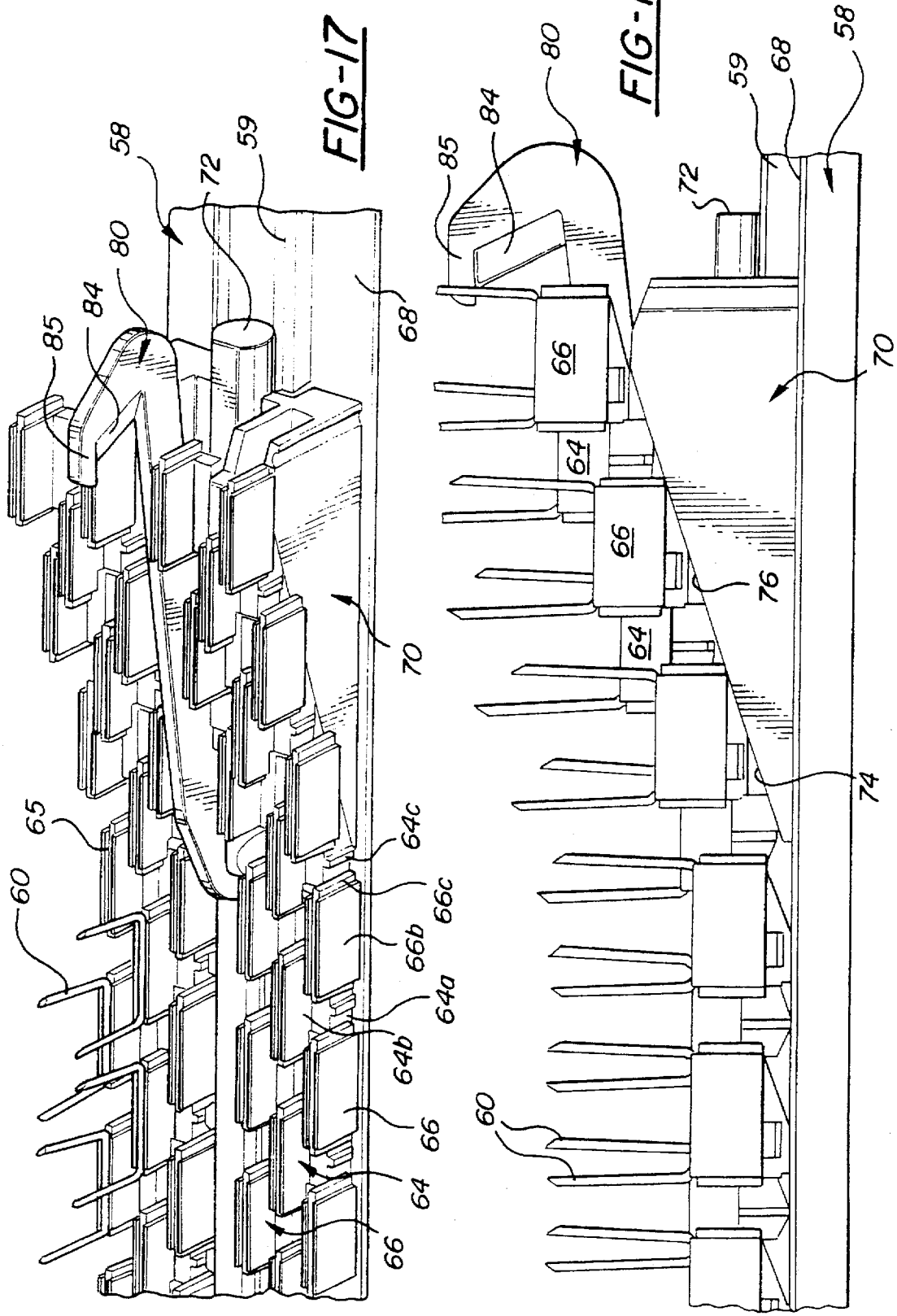

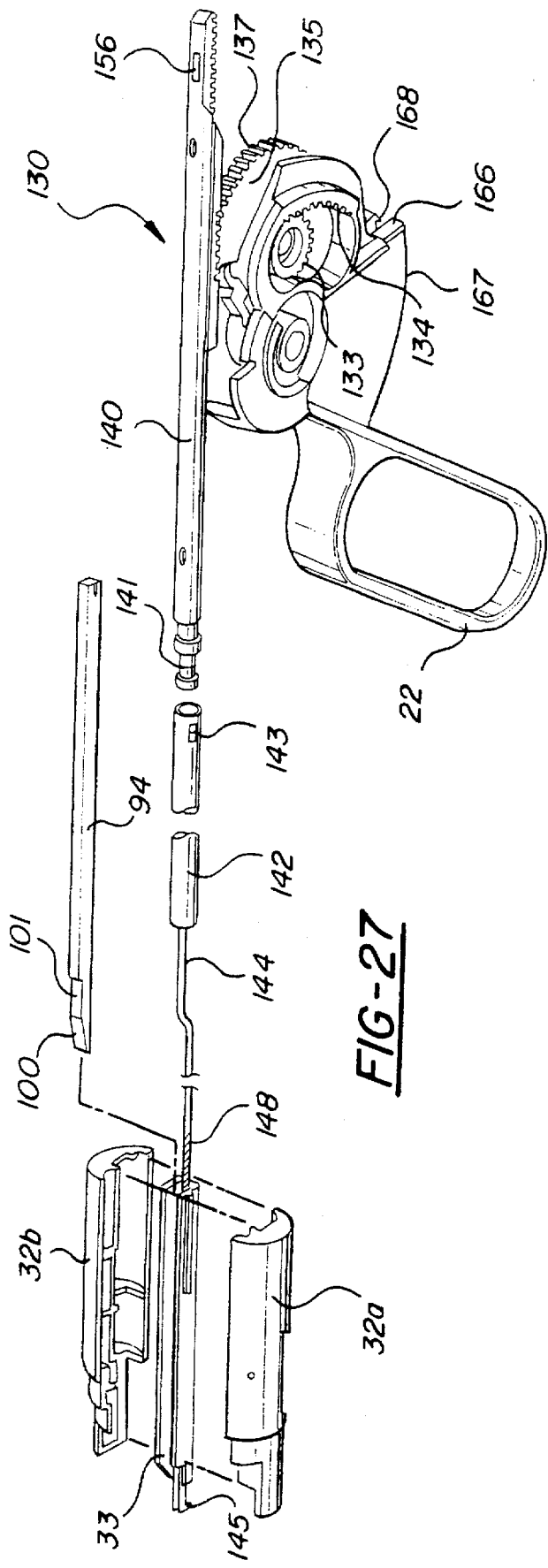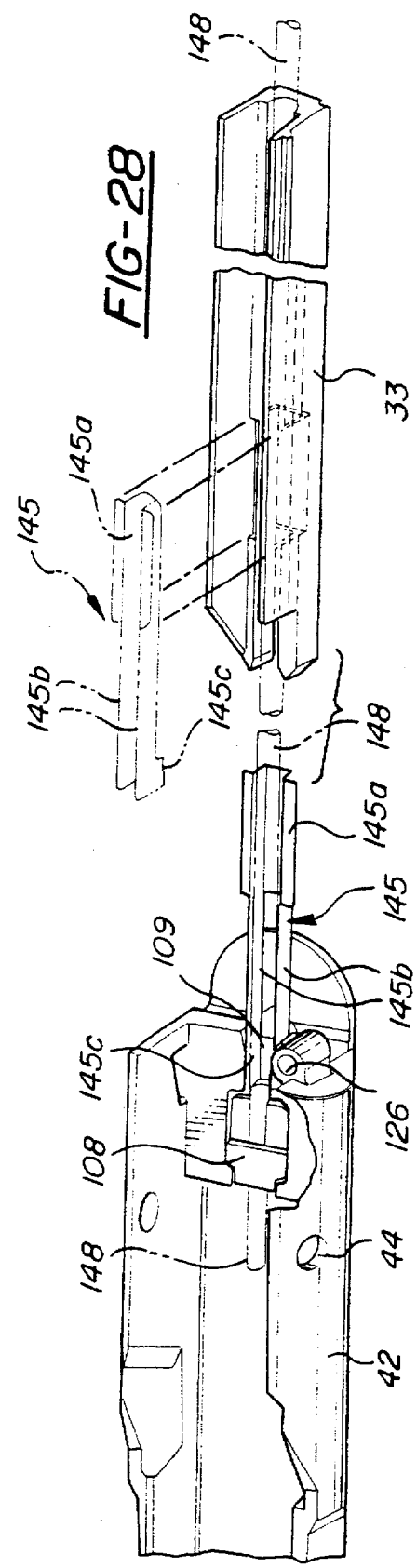

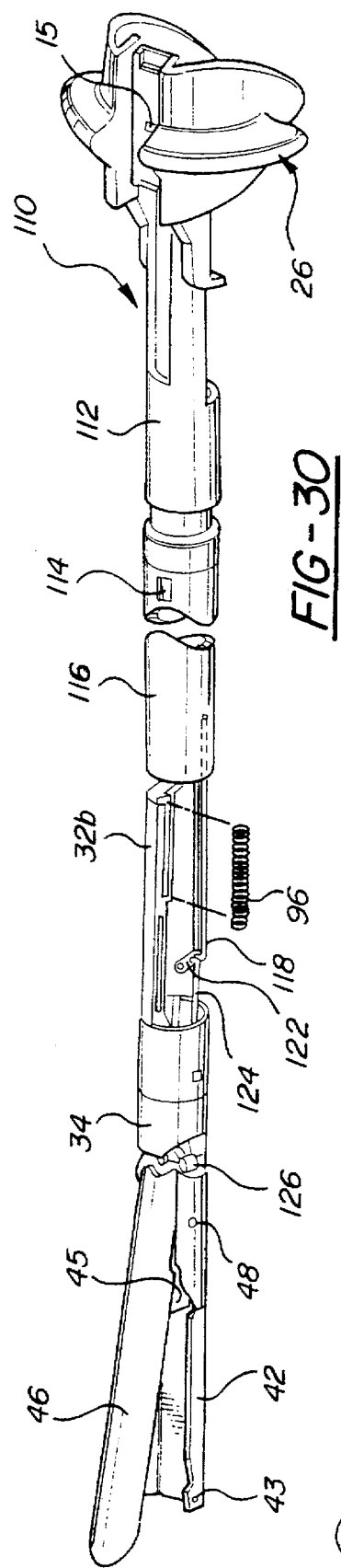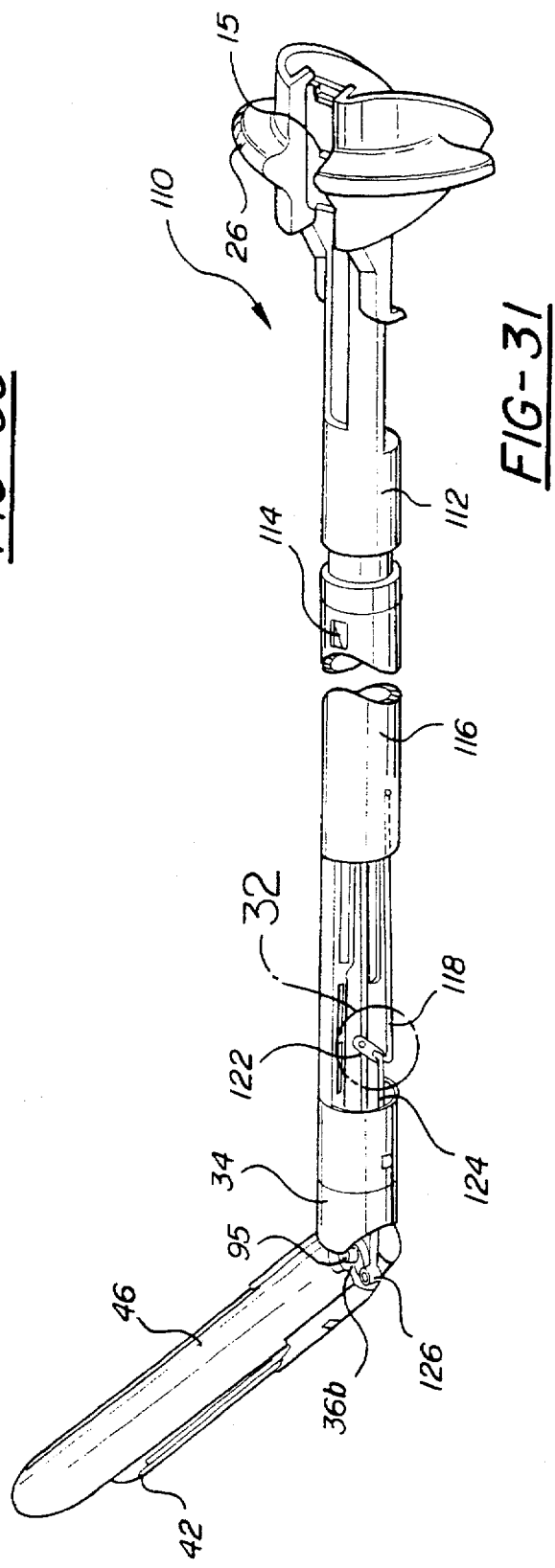

SURGICAL INSTRUMENT WITH IMPROVEMENT SAFETY LOCKOUT MECHANISMS

FIELD OF THE INVENTION

This invention relates generally to surgical instruments and, more particularly to laparoscopic surgical instruments having improved mechanisms for reducing the risk that the instrument will be improperly operated.

BACKGROUND OF THE INVENTION

There is always an inherent risk that surgical instruments will be used improperly despite the best intentions and training of surgeons. Surgical instruments also are becoming increasingly more complex as they are called upon to perform more operations and to do so with increasing flexibility. The increasing complexity of surgical instruments necessarily increases the challenges of operating the instruments.

Moreover, many surgical procedures traditionally were performed through a relatively large incision which opened up the operating site to direct observation by a surgeon. More recently, however, surgeons are developing new techniques that enable many "open" surgical procedures to be performed laparoscopically. In laparoscopic procedures, a few relatively small incisions are made in the body cavity. Smaller incisions greatly reduce trauma to a patient and speed recovery, and consequently, laparoscopic procedures represent a great improvement in the quality of surgical care that may be provided to patients.

Laparoscopic procedures, however, present additional challenges to a surgeon because a surgeon cannot directly observe the operation site or the instruments he is using. In laparoscopic procedures instruments are passed through elongated cylindrical tubes, known in the art as cannulas, which are placed in each incision and extend into the body cavity. The surgeon views the operation site on a video monitor via a miniature video camera which is inserted through one of the cannulas.

For example, bowel reconstruction is a procedure in which diseased portions of the bowel are removed. The bowel is a tubular shaped organ through which body wastes are processed. It is necessary to close off portions of the bowel before tissue is cut so as to minimize bleeding and discharge of bowel contents into a patient's body cavity.

One of the instruments commonly used in bowel reconstructions is a so-called linear stapler. Linear staplers are designed to form a row of staples through tissue. Thus, for example, portions of the bowel may be hemostatically closed by seams formed by such staple rows. Linear staplers also have been designed to close and divide tissue in a single operation. Such linear staplers form two parallel stapled seams and incorporate a cutting blade which then divides the tissue which is between the seams.

Linear staplers have been adapted for use in laparoscopic procedures. The typical configuration of such laparoscopic linear staplers in certain respects is similar to linear staplers designed for open surgery. The instrument generally includes a handle from which extends an elongated shaft. Controls are located on the handle so that a surgeon can manipulate and actuate the operating tip of the instrument.

The operating tip of the instrument does the actual stapling of tissue. Typically, it incorporates a pair of opposing jaws which clamp over the tissue to be stapled. One of the jaws includes a staple cartridge, usually a replaceable cartridge so that the instrument can be fired multiple times.

It is important that linear staplers be carefully placed in the proper position and that the laws be fully closed before the instrument is operated or "fired". Once the instrument is fired, especially when the stapler divides as well as staples, it may be difficult to repair damage which is caused by stapling or dividing tissue in the wrong place or by poor formation of staples. This is particularly true when a procedure is performed laparoscopically. Repairing such damage may require a large incision to open up the surgical site.

Similarly, when other types of surgical instruments are used, care must be taken to ensure that they are not fired at inopportune times or otherwise used improperly. For example, hernia staplers and other instruments are used to apply different types of staples and fasteners. Clip appliers are used to close tubes and ducts. If staples, clips, and the like are accidentally discharged into a patient's body cavity or applied in the wrong place, especially during laparoscopic procedures, it may be difficult to remedy such accidents.

Thus, continuing efforts have been made to reduce the risk that a surgeon will improperly use surgical instruments. For example, some early linear staplers designed for open surgery, such as those disclosed in U.S. Pat. No. 3,269,630 to H. Fleischer, utilized a mechanism which, in an initial range of operation, closes the jaws over tissue. Continued actuation of the mechanism through a further range of operation fires staples into the tissue. Since the jaws are closed and the staples fired by a common mechanism, it is impossible to fire the instrument unless the jaws are first closed.

The advantages to such designs are significant. The safety system is passive. That is, the design of the instrument ensures that the instrument cannot be fired when the jaws are open, and does so without requiring the surgeon to perform any special step. Using a single mechanism to close the jaws and to fire staples, however, is not particularly suited to laparoscopic linear staplers.

Laparoscopic linear staplers generally must be inserted through a cannula with the jaws in their closed position. Accordingly, if a single mechanism is used to close the jaws and to fire staples there is a risk that staples will be partially fired when the jaws are closed to insert the instrument. Further, even in open surgery, a surgeon may prefer to lock down the jaws and then pause momentarily to ensure the jaws are clamped exactly in the right place.

Other linear staplers have separate mechanisms for closing the jaws and firing the staples, and such staplers have incorporated passive safety systems which prevent firing unless the jaws are properly closed. Those systems reflect two general approaches: one approach utilizes a normally disengaged firing mechanism which is engaged when the jaws are closed; the other approach utilizes a normally immobilized firing mechanism which is released when the jaws are closed.

For example, U.S. Pat. No. 5,397,046 to R. Savage et al. discloses a linear stapler which has a gas powered firing mechanism and utilizes a lever to actuate a mechanism which closes the instrument's jaws. The firing mechanism is normally disengaged. It remains disengaged unless the lever is pivoted to close the jaws. As the lever is pivoted, it shifts a pivoting transmission link into engagement with the rest of the firing mechanism.

Another instrument using the same general approach is disclosed in U.S. Pat. No. 4,383,634 to D. Green. The linear stapler disclosed therein utilizes a lever to close the jaws. The lever carries with it a drive shaft, and as the lever pivots to close the jaws, it brings the drive shift into engagement with the rest of the stapler's firing mechanism. In the absence of the drive shaft, the firing mechanism is disengaged and inoperable.

U.S. Pat. No. 5,425,745 discloses a passive lockout system which immobilizes the firing mechanism unless the jaws are properly closed. The stapler disclosed therein has a firing mechanism which includes a reciprocating drive shaft mounted in the handle. A leaf spring normally engages the drive shaft, thus locking up the firing mechanism and preventing the instrument from being fired.

The stapler's jaw closure mechanism has a pivoting lever which is connected to another reciprocating drive shaft. When the lever is pivoted to close the jaws, the second drive shaft is moved forward, carrying with it a release which forces the spring out of engagement with the firing mechanism drive shaft. The firing mechanism is thereby released so that the instrument can be fired.

Such leaf springs are machined from tempered steel, and it is relatively difficult to manufacture such springs to exact tolerances. Moreover, when they are assembled into a mechanism, such springs are subject to additional variation in their fit and interaction with other components. Such factors may introduce less than desirable control over the assembly of the instrument and the operation and timing of passive lockout mechanisms.

Linear staplers also have utilized various trigger safety mechanisms, either alone or in combination with other types of safety systems. Those trigger safeties provide an active safety system, that is, they immobilize the trigger of the stapler until they are deactivated by a surgeon.

Trigger safeties are widely utilized in instruments having a pistol-type handle, which is the most common type of handle in current use. Although not without some variation, pistol handles typically have a stationary grip and a pivoting trigger. In their simplest form such trigger safeties constitute a pivoting arm which extends from the grip and bears against the inside of the trigger as disclosed, for example, in the '634 patent. The safety is released by pivoting the arm away from the trigger so that it no longer blocks the trigger's movement toward the grip. U.S. Pat. No. 4,591,085 to J. Di Giovanni and U.S. Pat. No. 4,527,724 to H. Chow et al. both disclose open linear staplers having trigger safeties of this type which cannot be released until the jaws are closed.

The trigger safeties in all of those instruments, however, must be manually reset each time the instrument is fired. If a surgeon forgets to reset the trigger safety, there is a risk the surgeon may fire the instrument unintentionally. Even if the instrument incorporates a passive system to prevent firing unless the jaws are closed, the jaws of a laparoscopic stapler generally must be closed to insert the instrument through a cannula. Thus, the instrument will be activated each time it is passed through a cannula, and there will be a risk of unintentional firing of the stapler as it is handled.

The laparoscopic linear stapler disclosed in the '046 patent has a different type of trigger and safety. The stapler has a grip, but it is fired by depressing a trigger button located on the heel of the grip. A rotary safety button is mounted through the trigger button, and it is biased towards a locked position in which it prevents the trigger button from being depressed. The safety button may be manually rotated to a release position and held there while the trigger button is depressed to fire the instrument.

While this trigger safety mechanism offers the advantage of automatically resetting, it requires excessive dexterity and coordination to use. Moreover, it is uniquely adapted for use with push button triggers, and it cannot be incorporated into instruments using more popular pivoting triggers.

Further, many surgical instruments are very complex and incorporate many different mechanical systems. For example, some proposed laparoscopic linear staplers include jaw closure mechanisms, firing mechanisms, articulation mechanisms, and various rotational mechanisms. Especially under such circumstances, existing lockout mechanisms may needlessly increase the complexity of an instrument and require excessive modification of the primary mechanical systems present in the instrument.

Existing surgical instruments have not satisfactorily addressed such problems. It is, therefore, a general object of the invention to provide improved surgical instruments and, especially, improved linear staplers, hernia staplers, and clip appliers for use in laparoscopic procedures. A more specific object is to provide such instruments with improved active and passive safety mechanisms to increase the likelihood that an instrument will not be misoperated. A related object is to provide such safety mechanisms which decrease the likelihood that an instrument will be fired unintentionally when it is being handled during surgery or when its operating tip is not properly positioned on the target tissue.

Another object is to provide such safety mechanisms which are of relatively simple designs and are compatible with other mechanisms incorporated into an instrument. A related object is to provide such safety mechanisms which may be easily and economically manufactured.

A further object is to provide active safety mechanisms which may be operated more easily and reliably by surgeons. A related object is to provide improved active safety mechanisms which can be used in instruments having pistol grips and pivoting triggers.

Yet another object of the subject invention is to provide surgical instruments wherein all of the above mentioned advantages are realized.

Those and other objects and advantages of the invention will be apparent to those skilled in the art upon reading the following detailed description and upon reference to the drawings.

SUMMARY OF THE INVENTION

This invention provides for surgical instruments including an operating mechanism for repeatedly performing a surgical procedure and a control mechanism for manipulating the instrument between a neutral position and a ready position for performing the surgical procedure. The instruments comprise a passive lockout assembly and an active lockout assembly.

The passive lockout assembly includes a key. The key is operatively connected to the control mechanism for reciprocating movement between a first position corresponding to the neutral position of the instrument and a second position corresponding to the ready position of the instrument. In its first, neutral position the key immobilizes the operating mechanism, thereby preventing the instrument from performing the surgical procedure. In its second, ready position the key releases the operating mechanism.

The active lockout assembly includes a plunger. The plunger is operatively connected to a manually operable switch for reciprocating movement between a first position and a second position. In its first position the plunger immobilizes the operating mechanism, thereby preventing the instrument from performing the surgical procedure. In its second position the plunger releases the operating mechanism. The plunger is movable to its second position by manual operation of the switch, but is biased toward its first position such that it returns to its first position after actuation of the operating mechanism.

Each time the instrument is used to perform the surgical operation, therefore, the instrument must be in the ready position and the active lockout switch must be operated. Otherwise, the operating mechanism of the instrument is immobilized by one or both of the passive and active lockout assemblies.

This invention also provides for such instruments which have a passive lockout assembly. In accordance with this aspect of the invention, the instruments generally include a handle, an actuator, and a pivoting key.

The actuator is pivotally mounted to the handle by a pivoting link for pivoting motion between a first and a second position. The actuator also is operatively connected to the control mechanism such that movement of the actuator from its first to its second position causes the control mechanism to manipulate the instrument from its neutral to its ready position.

The pivoting key is operatively connected to the link. It pivots between a first position corresponding to the actuator first position and a second position corresponding to the actuator second position. In its first position the key immobilizes the operating mechanism, and in its second position the key releases the operating mechanism. Consequently, the operating system is immobilized by the key when the instrument is in its neutral position.

This invention further provides for surgical instruments which have an operating mechanism for performing a surgical procedure and an active lockout mechanism. In accordance with this aspect of the subject invention, the novel instruments generally comprise a handle, an actuator, a latch, a plunger, and a switch.

The actuator is mounted on the handle for reciprocating movement between a first position and a second position. The actuator is operatively connected to the operating mechanism such that movement of the actuator from its first position actuates the operating mechanism and causes it to perform the surgical procedure.

The latch is mounted in the handle for reciprocating movement between a first position and a second position. The latch is biased toward its first position.

The plunger is mounted in the handle for reciprocating translational movement between a first position and a second position and is biased towards its first position. In its first position the plunger engages the actuator in its first position, thereby preventing the actuator from actuating the operating mechanism. When the plunger is in its first position it also engages the latch and holds the latch in a position intermediate to its first and second positions.

The manually operated switch is operably connected to the plunger such that operation of the switch moves the plunger from its first to its second position. In its second position the plunger disengages the actuator.

Movement of the plunger from its first position to its second position allows the latch to move from its intermediate position to its first position. When the latch is in its first position it engages the plunger, the latch, thereby holding the plunger in its second position. In turn, the plunger allows movement of the actuator from its first position to actuate the operating mechanism.

Subsequent movement of the actuator from its first position towards its second position moves the latch from its first position towards its second position. In its second position the latch is clear of the plunger path. Thus, the latch allows the plunger to move from its second position to an intermediate position in which it is clear of the path of the actuator and interposed in the return path of the latch.

Subsequent movement of the actuator back towards its first position allows the plunger to move from its intermediate position back to its first position. When it returns to its first position the actuator again prevents the actuator from actuating the operating mechanism. Consequently, the switch must be manually operated each time the actuator is returned to its first position.

As will become apparent from the detailed description which follows, the novel instruments incorporate passive and active lockout systems which, alone and in combination, increase the likelihood that the instrument will not be misoperated. In particular, the improved lockout mechanisms decrease the likelihood that an instrument will be fired unintentionally as it is handled during surgery or when it is not properly positioned on the target tissue.

BRIEF DESCRIPTION OF THE DRAWINGS

FIG. 4 is a front elevational view of instrument 10;

FIG. 5 is a rear elevational view of instrument 10;

FIG. 6 is a top plan view of instrument 10;

FIG. 7 is a bottom clan view of instrument 10;

FIGS. 8A and 8B (collectively FIG. 8) constitute an exploded, left side perspective view of the handle assembly 20 and certain components of the shaft assembly 30 of instrument 10;

FIG. 9 is an exploded, left side perspective view of the tip assembly 40 of instrument 10;

FIG. 10 is a left side, bottom perspective view of the anvil 46 of instrument 10;

FIG. 11 is a top, left side perspective view of the cartridge assembly 50 of instrument 10;

FIG. 12 is a left side, bottom perspective view or the cartridge housing shroud 56 of instrument 10;

FIG. 13 is a top, side perspective view of a single staple driver 64 of instrument 10;

FIG. 14 is a top, right side perspective view of a double staple driver 66 of instrument 10.

FIG. 15 is left side, front, top perspective view of the double staple driver 66 shown in FIG. 14;

FIG. 16 is an exploded, top, left side perspective view of the staple cartridge sled 70 of instrument 10 including a knife 80;

FIG. 17 is a rear, left side, top perspective view of selected components of the cartridge assembly 50 of instrument 10;

FIG. 18 is a side elevational view of the cartridge assembly 50 components shown in FIG. 17;

FIGS. 19–21 are rear, left side, top perspective views of the sled 70 shown in FIG. 16, showing in particular the sled knife 80 in its various positions;

FIG. 27 is a partially exploded, top perspective view of the firing system 130 and selected other components of instrument 10;

FIG. 28 is a partially exploded, top perspective partial view of selected components of the shaft 30 and tip 40 assemblies of instrument 10, showing in certain components supporting the drive cable 148 of the firing system 130;

FIG. 29 is a side elevational, partial view similar to FIG. 28 showing selected other components supporting the drive cable 148 of firing system 130;

FIG. 30 is a partially exploded, top, side perspective view of the articulation control system 110 and selected other components of instrument 10, showing the tip 40 in its unarticulated position;

FIG. 31 is a view similar to FIG. 30, showing the tip 40 in an articulated position;

DESCRIPTION OF THE PREFERRED EMBODIMENTS

A laparoscopic instrument 10 constructed in accordance with the teachings of the instant invention is shown generally in FIGS. 1–7. The illustrated embodiment 10 of the invention is configured as a laparoscopic, articulated linear stapler which is capable of both stapling and cutting tissue. The subject invention is particularly useful in the context of such instruments because the instrument is subject to a great deal of manipulation prior to firing, and it is extremely important that the instrument not be fired until the jaws are properly closed over the appropriate tissue.

Those skilled in the art will readily appreciate, however, that the invention is not limited to the disclosed linear stapler 10 in particular or to linear staplers in general. On the contrary, the teachings of the instant invention can be employed in surgical instruments of widely varying designs, purposes, and uses without departing from the scope or the spirit of the invention. The subject invention, as will become apparent from the discussion which follows, can be applied to any instrument having two mechanisms which must be operated in a particular sequence or to instruments which have a pistol-type handle with a pivoting trigger. Moreover, while the need for safety mechanisms is more acute in laparoscopic instruments and, thus, the invention is particularly useful in laparoscopic instruments, the invention can be applied to surgical instruments designed for open procedures as well. For example, hernia staplers, clip appliers, and cutters can be constructed in accordance with the subject invention.

Figure 1:
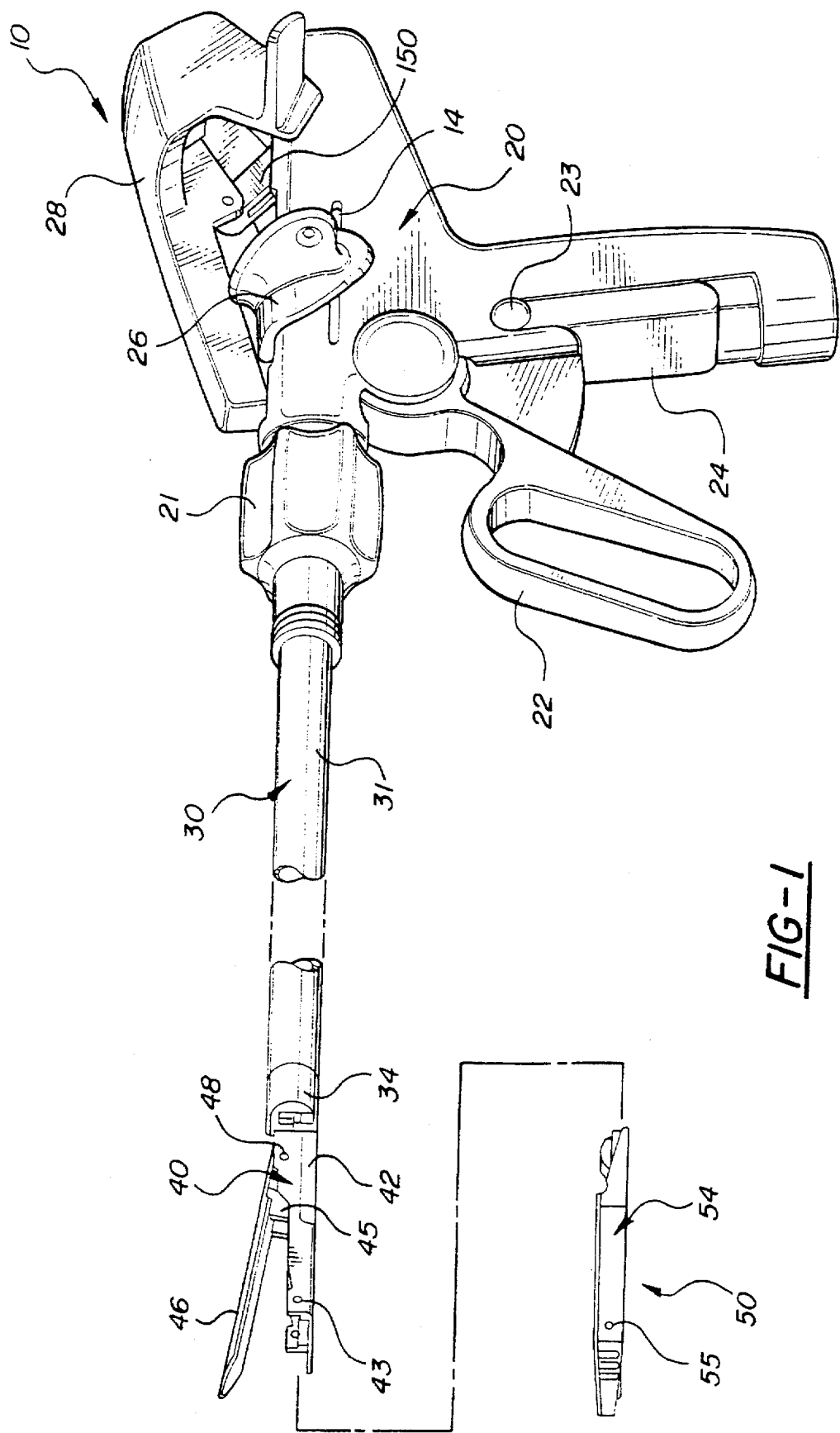
FIG. 1 is a front, left side and partially exploded perspective view of a preferred embodiment 10 of the subject invention, wherein instrument 10 is a laparoscopic linear stapler/divider with a rotating shaft and an articulating tip having replaceable staple cartridges.
Figure 2:
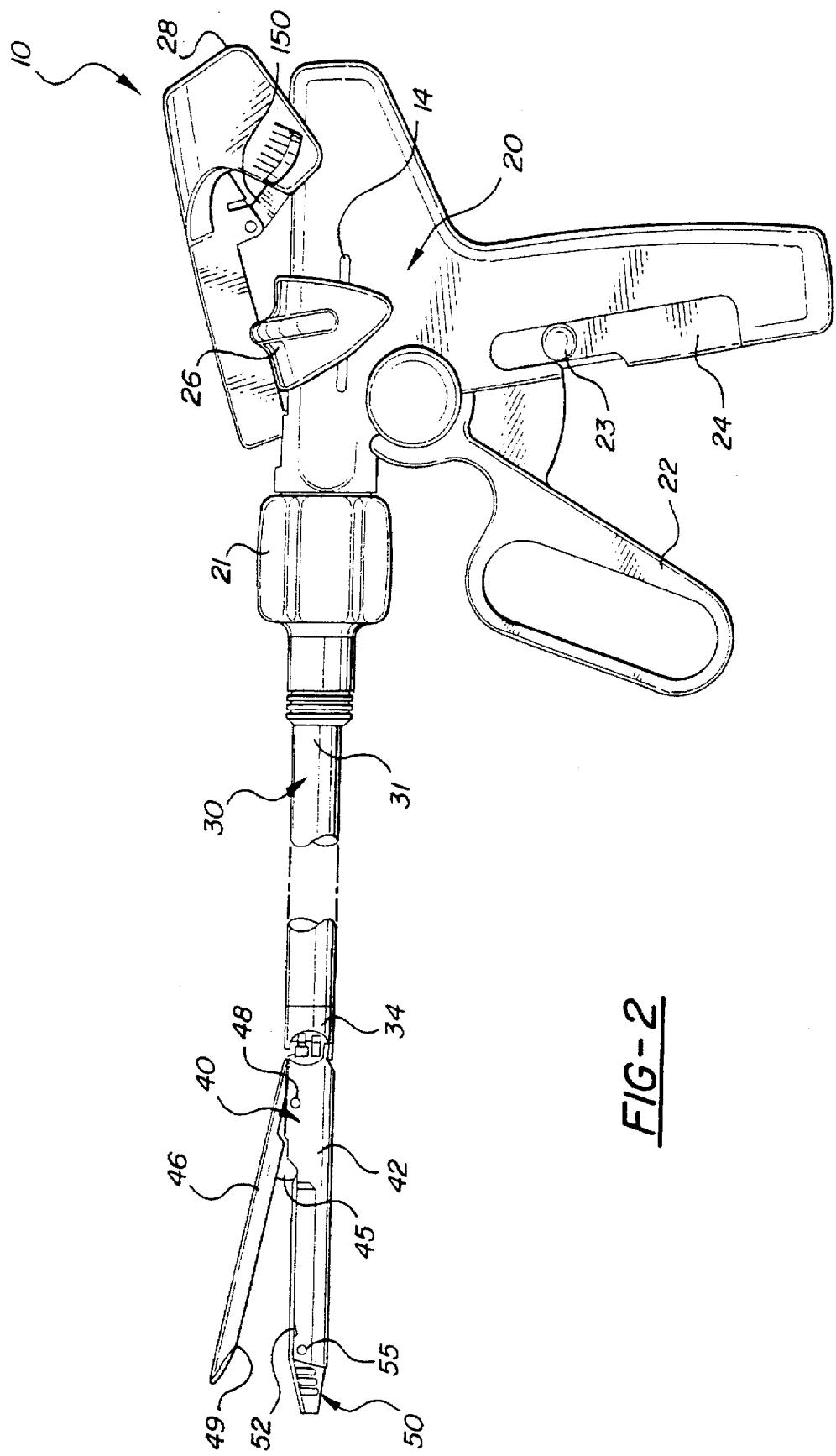
FIG. 2 is a left elevational view of instrument 10 showing the instrument 10 with its jaws in the open position.
Figure 3:
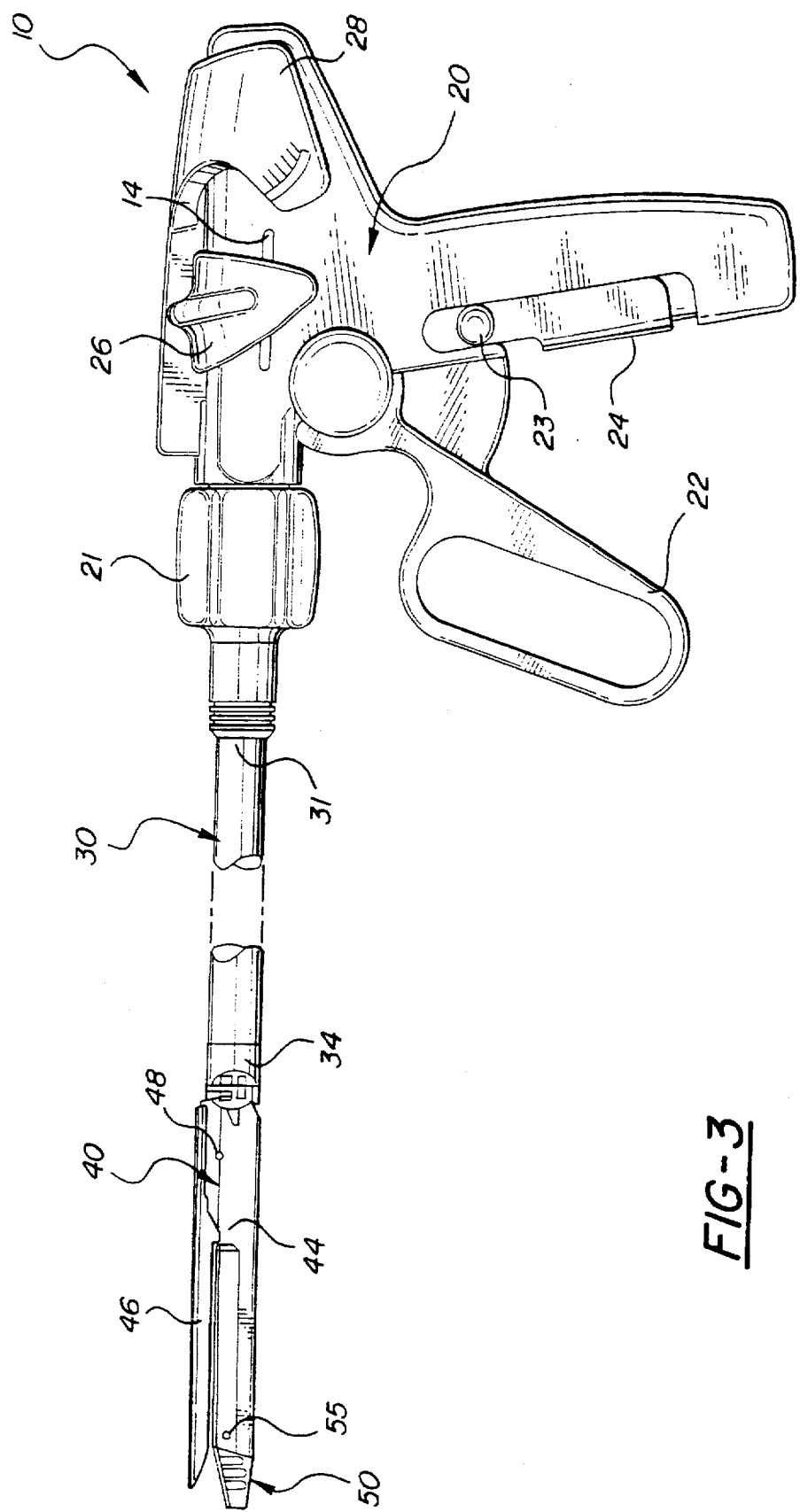
FIG. 3 is an elevational view similar to FIG. 2, but showing the instrument 10 with its jaws in the clamped or closed position.

The laparoscopic instrument 10, as best seen in FIGS. 1–3, generally includes a handle 20, an elongated shaft 30, and a tip 40. In general, the handle 20 allows a surgeon to comfortably grasp the instrument 10 and provides the surgeon with easy access to the controls or actuators which can be manipulated to operate the various mechanical systems incorporated into the instrument 10. For example, as shown in FIG. 2, the handle 20 includes the following actuators: a rotation knob 21 which a user can manipulate to rotate the shaft 30 about its longitudinal axis; a firing trigger 22 to actuate a firing system; a safety switch 24 to release a safety lockout system so the firing system can be actuated; an articulation slide 26 to actuate an articulation system; and a clamp-up lever 28 to actuate a jaw closure system.

The overall shape of the handle is determined in large part by the usual ergonomic considerations. Accordingly, the handle 20 in the illustrated embodiment is configured as a pistol-type grip which can be easily manipulated by a surgeon. As will become apparent from the discussion which follows, certain aspects of the invention, i.e., the novel active safety lockout systems described herein, are particularly suited to instruments having a pistol grip and a pivoting trigger. Those skilled in the art will readily appreciate, however, that other handle designs are known and can be employed consistent with other aspects of the invention. Similarly, although the various actuators associated with the handle 20 have been illustrated and are particularly suited to certain aspects of the invention, those skilled in the art will appreciate that other types of actuators with different ergonomic or operating characteristics could be substituted for the illustrated actuators in other aspects of the invention. Once ergonomic and operating criteria are met, however, there remains considerable room to provide a variety of ornamental details which enhance the aesthetic appeal of the instrument.

The handle 20 also houses and supports various components of the instrument's mechanical systems. To this end, the handle 20 preferably comprises two molded plastic halves 25, 27, as shown in FIG. 8, which include various projections, openings and other design features that support and interact with the mechanical systems as further described below.

The elongated shaft 30, which includes a proximal end coupled to the handle 20 and a distal end coupled to the tip 40, performs several functions. First, like the handle 20, the shaft 30 provides a housing for various components of the mechanical systems of the instrument 10. Accordingly, the shaft assembly 30 includes an outer shaft tube 31 which is generally open at each end. The proximal end of shaft tube 31 is connected to the rotation knob 21 via connector 38 and washer 39, as can be appreciated from FIG. 8A, connector 38 having a pair of arms which snap into suitable openings in rotation knob 21. A clevis body 32 comprising clevis halves 32a and 32b shown in FIG. 27 is disposed in the shaft tube 31 near its distal end. An insert 33 in turn is disposed in the clevis body 32. An end piece 34 shown, e.g., in FIGS. 1 and 30 is mounted over the distal end of the shaft tube 31. The shaft tube 31, the clevis body 32, the clevis body insert 33, and the shaft end piece 34, as will be apparent from the discussion which follows provide support for and/or accommodate various components of the instrument's mechanical systems.

The shaft 30 also extends the tip 40 a distance from the handle 20 sufficient to enable a surgeon working outside a patient's body to reach and manipulate tissue in the patient's body cavity. In order to permit the instrument 10 to be used through a trocar cannula or the like, the elongated shaft 30 preferably is substantially cylindrical. In the preferred embodiment, the shaft 30 is about 315 mm long. Preferably, the cross-section diameter of the shaft 30 is chosen to enable the instrument 10 to be used with commercially available cannulas. For example, many commercially available cannulas have nominal diameters of 5 mm, 6 mm, 8 mm, 10 mm, 10.5 mm, 12 mm, or 18 mm. The diameter of the shaft 30 preferably will be chosen with the dimensions of those commercially available cannulas in mind.

In order to provide greater accessibility to tissue in a body cavity and to enable a surgeon to comfortably manipulate that tissue, the shaft 30 preferably is rotatable relative to the handle 20. In order to facilitate this rotation, the shaft 30 is provided with the rotation knob 21, as shown in FIG. 1. Rotating knob 21 will rotate the shaft 30 by a like amount. The knob 21 is disposed at the distal end of the handle 20 so that it is easily accessible to a surgeon. As will be appreciated from FIG. 8B, the handle 20 on the distal end of handle half 27 by collar 19, such that the distal end of resilient member 17 mates with a plurality of notches (not shown) formed in the inner surface of the knob 21 to hold the shaft 30 in discrete positions relative to the handle 20 as it is rotated.

While rotation of the shaft relative to the handle is preferred, instruments constructed in accordance with the subject invention may incorporate fixed shafts. Similarly, the precise manner in which the shaft is rotatably coupled to the handle forms no part of the subject invention. The rotational coupling of the shaft and the various mechanisms passing through that coupling disclosed herein are believed to contribute to the efficient construction and operation of the instrument, but other such couplings may be used.

The operating tip 40 of the instrument 10 is designed to clamp over and then to staple and divide tissue. Accordingly, the tip 40 has a pair of opposed jaws, namely, an anvil 46 and a receiver 42, which are pivotally coupled together, as shown in FIG. 1. The receiver 42 is an elongated arm-like structure having a U-shaped cross-section, as better seen in FIG. 9, which is designed to slidably receive a removable staple cartridge assembly 50, as shown in FIG. 1. The cartridge 50 delivers staples and divides tissue as described in further detail below.

The anvil 46 also is an elongated arm-like structure. The anvil 46 has staple forming recesses 61 in its lower surface 49, as seen best in FIG. 10. Staples are ejected from the cartridge 50, as described in further detail below, and are formed against the recesses 61.

Tissue is secured between the lower surface 49 of the anvil 46 and an upper surface 52 of the cartridge 50 before the tissue is stapled and divided. To this end, the anvil 46 and the receiver 42 each include a pair of aligned bores 44 located near their proximal ends, as shown in FIG. 9. A pin 48 passes through the bores 44 of the anvil 46 and the receiver 42. Pin 48 secures the jaws 42, 46 together in such a manner that they may be moved between an open position shown in FIG. 2 and a closed position shown in FIG. 3.

As will become more apparent from the discussion which follows, the invention in its broadest aspects encompasses various instruments other than articulated linear staplers. Consequently, the invention is not limited to instruments having operating tips such as tip 40. For example, the tip could be configured to apply a staple without clamping, over tissue, as is common in hernia staplers.

Likewise, when linear staplers are constructed in accordance with the subject invention, the specific manner in which the jaws are coupled together is merely a preferred aspect of the subject invention. The jaws need not be pivotally coupled as in the illustrated embodiment, and indeed, they need not be configured as pivoting jaws. Other mechanisms for allowing cooperative movement between jaws are known and may be used if desired.

The tip 40 of the instrument 10 is pivotally coupled to the distal end of the shaft 30 for articulation at an articulation joint. More particularly, anvil 46 is provided with an articulation bore 47 as shown in FIG. 9. The shaft assembly 30 is provided with a like pair of articulation bores, specifically, a bore 37 in a leaf spring 36 extending through shaft end piece 34 and a bore 35 disposed on the opposite side of the distal end of shaft end piece 34, as shown in FIG. 29. As will be appreciated by comparing FIGS. 9 and 29, a pin 95 passes through bore 47 on anvil 46 and bore 37 in leaf spring 36. Similarly, a post 107 extends from receiver 42 and passes through bore 35 on shaft end piece 34. Thus, the tip 40 may articulate relative to the shaft 30 about an articulation axis passing generally through bores 47, 37, 35, pin 95, and post 107.

Consequently, a surgeon is able to reach more areas in a patient's body cavity more easily. The tip, however, need not be articulated relative to the shaft. The subject invention encompasses instruments having fixed tips. Likewise, if the tip is articulated, the precise manner in which the tip is coupled to the shaft for articulation is not part of the subject invention. The tip may be coupled to the shaft for articulation by whatever means are desired, especially when different jaws are utilized. For example, the jaws may be constructed such that only one jaw is directly coupled to the shaft for articulation.

The illustrated linear stapler 10 is designed to form two parallel, hemostatic stapled seams and to divide the tissue between the seams in a single operation. Accordingly, cartridge assembly 50 includes a housing 54, a plurality of staples 60, a plurality of staple drivers 64, 66, and a movable sled 70 having a cutting knife 80 as illustrated in FIGS. 9–21. As will be explained in further detail below, the moveable sled 70 sequentially actuates the staple drivers 64, 66 which in turn drive staples 60 out of the cartridge, through the tissue, and against the anvil 46. The knife 80 moves with the sled 70 to divide the tissue shortly after the stapled seams are formed.

Housing 54 comprises two components, namely, a shroud 56 and a base 58 which collectively define a central cavity and various other openings, tracks, and supports designed to accommodate the other components of the cartridge assembly 50. The shroud 56 has the upper surface 52 referred to above. The upper surface 52 extends between the proximal and distal ends of the shroud 56 parallel to the longitudinal axis of the shroud 56, as can be seen in FIG. 9. The upper surface of base 58 provides a floor 68 which extends generally parallel to and below the upper surface 52 of shroud 56. The base 58 and shroud 56 define a central cavity through which, as described in further detail below, sled 70 may travel As shown in FIG. 9, the housing shroud 56 defines a plurality of staple openings 51. Each of the staple openings 51 frictionally holds a staple 60 such that the tips of the staples 60 are disposed near the upper surface 52 of the shroud 56. The staple openings 51 provide passageways for upward movement of staples 60 from the cartridge assembly 50 into tissue clamped against the upper surface 52 of the shroud 56.

The staple openings 51 are arranged in two spaced sets such that staples 60 ejected therefrom will form two parallel stapled seams. Each set includes three parallel rows of staple openings 51. Two of the rows, one in each set, are staggered with respect to the other four rows to facilitate the formation of hemostatic seams.

A staple driver 64, 66 is associated with each staple 60 and staple opening 51, as best appreciated by comparing FIGS. 9, 12 and 17–18. The plurality of drivers 64, 66 include two types of drivers, namely, single staple drivers 64 and double staple drivers 66 as shown in FIG. 13–15. As their names suggest, the single staple drivers 64 are designed to drive one staple 60 and the double staple drivers 66 are designed to simultaneously drive two staples 60. As illustrated in FIG. 13 the single staple driving members 64 include a base 64a supporting an integral plate 64b extending upwards from and across the base 64a on or about its lateral midpoint. The bottom of the base 64a provides a camming surface which, as described in further detail below, interacts with the sled 70. The upper surface of plate 64b defines a U-shaped staple trough 65 which receives and supports an inverted staple 60 as shown in FIGS. 17–18. In contrast as shown in FIGS. 14–15, the double staple drivers 66 include a base 66a with two integral plates 66b extending upwards from the edges of base 66a. The bottom of base 66a provides a camming surface, and the upper surface of each plate 66b defines a staple trough 65.

The staple drivers 64, 66 are arranged in two parallel rows, one row on either side of the longitudinal center plane of the housing 54, as can be seen in FIGS. 17–18. Each row of staple drivers 64, 66 includes alternating single staple drivers 64 and double drivers 66 arranged such that the plates 64b of the single drivers 64 extend upwards in a staggered fashion between the plates 66b of the double drivers 66. The bases 64a, 66a of the staple drivers 64, 66 are arranged end to end such that the lower camming surfaces thereof are aligned.

As will be more fully appreciated from the description which follows, each row of staple drivers is associated with one of the stapled seams which are formed by instrument 10. The single staple drivers 64 in each row drive the staples 60 in the offset, middle row of each set of staple openings 51. The double staple drivers 66 drive the staples 60 in the outer rows of each set of staple openings 51.

The cartridge assembly 50 also includes the moveable sled 70 mentioned above. Sled 70 is adapted to actuate the staple drivers as it travels distally through the cartridge assembly 50. Accordingly, as best shown in FIG. 16, the preferred embodiment of sled 70 generally has a wedge-shaped body. More particularly, the sled 70 has two relatively wide, leading ramped upper surfaces 74. Each leading ramped surface 74 leads into two, relatively widely spaced, narrower trailing ramped surfaces 76. The ramped surfaces 74, 76 sequentially cam under staple drivers 64, 66 thereby translating the distal motion of the sled 70 to upward motion of the staple drivers 64, 66.

More particularly when the cartridge 50 in its initial, "loaded" state, sled 70 is situated generally at the proximal end of cartridge 50. Staple drivers 64, 66 are adjacent the floor 68 of housing 54, and staples 60 are disposed within the staple openings 51. As the instrument is fired, the sled is driven distally by a firing system which is described in further detail below.

As best appreciated from FIGS. 17–18, when the sled 70 travels distally through the cartridge 50, the leading ramped surfaces 74 contact the bases 66a of the most proximal double staple drivers 66 in each set of staple drivers 64, 66. The sled 70 continues forward and begins camming those most proximal double staple drivers 66 upward, and the double staple drivers 66 in turn begin driving their associated staples out of the staple openings 51 toward the anvil 46. The proximal side of the bases 66a of double staple drivers 66 are ramped at an angle complementary to the ramped upper surfaces 74, 76 of sled 70 to facilitate this camming action.

The staple drivers 64, 66 in each row are arranged in an end-to-end fashion such that the base 66a of a double staple driver 66 is overlapped by the plates 64b of single staple drivers 64 adjacent to the double staple driver 66. In order to ensure that the double staple drivers 66 are not hindered in their upward movement by this overlap, and that they move independently of single staple drivers 64, the bases 66a of the double staple drivers 66 each are provided with a recess 67 in the distal side of their upper surface, as seen best in FIG. 15. Recesses 67 provide clearance between the base 66a of a double staple driver 66 and the overlapping plate 64b of the single staple driver 64 distal thereto. In other words, as a double staple driver 64 moves upwards, the recess 67 accommodates the overlapping portion of the plate 64b of the as yet undisplaced single staple driver 64 which is located distally thereto thereby ensuring that the double staple driver 66 does not engage and displace the single staple driver 64 as it is cammed upwards by the sled 70.

As the sled 70 continues through the housing 54 in the distal direction it then contacts the most proximal single staple drivers 64 in each row of staple drivers 64, 66 and begins camming them upward. The proximal side of bases 64a of single staple drivers 64 also are ramped in a manner similar to the bases 66a of double staple drivers 66 to facilitate this upward camming. The sled 70 continues traveling distally, thereby sequentially camming a pair of double staple drivers 66 (one in each row of staple drivers 64, 66), a pair of single staple drivers 64, and so on until, by the time the sled 70 has reached its distalmost position all staple drivers have been driven completely upward such that the plates 64b, 66b extend into the staple openings 51 and have fully ejected all staples 60.

The shroud 56 and base 58 collectively define openings and tracks for the respective movement of the sled 70 and staple drivers 64, 66. More particularly, the shroud 56 includes a plurality of columns 57 as shown in FIG. 12. Columns 57 extend generally downward from shroud 56 adjacent to staple openings 51 and are arranged in six parallel rows. The two outer rows of columns 57a, 57f are disposed adjacent the walls of the housing 54. The four inner rows of columns 57b, 57c, 57d, 57e are disposed between the outer walls.

The columns 57 have different lengths depending upon their location within the housing 54. Specifically, the columns 57a, 57f located in the outer rows adjacent the walls of the shroud 56 extend from the top of the shroud 56 to the floor 68 whereas the columns 57b, 57c, 57d, 57e in the four inner rows terminate before reaching the floor 68. Thus, an opening or distance which extends substantially the length of the cartridge is formed between the bottom of the columns 57b, 57c, 57d, 57e in the inner rows and the floor 68. It will be appreciated that this opening accommodates passage of the lower portion of sled 70 as it moves distally through the cartridge.

Columns 57 also are adapted to provide tracks for the staple drivers 64, 66 as they are cammed upward by sled 70.

Accordingly, columns 57 are provided with channels in their proximal and distal ends which mate with projections 64c, 66c on each end of the plates 64b, 66b of the staple drivers 64, 66 as may be seen by comparing FIGS. 12-15. Likewise, the sides of columns 57a, 57c, 57d, 57f are provided with channels which mate with similar projections 64c on the ends of base 64a of the single staple drivers 64. The bases 66b of double staple drivers 66 have a passageway (not shown) through which columns 57b, 57e extend. The interaction of the drivers 64, 66 and their projections 64c, 66c with the columns 57 and their channels serve to maintain the alignment of the drivers 64, 66 as they drive their associated staples 60 out of the cartridge assembly 50.

In order to insure the staples 60 driven out of the cartridge assembly 50 are properly formed, the anvil 46 which clamps tissue against the upper surface 52 of the shroud 56 is provided with staple forming recesses 61 having inwardly sloped surfaces as shown in FIG. 10. When the anvil 46 is pivoted to the clamped position, recesses 61 are aligned with the staple openings 51. As a result, when staples 60 are driven through and out of the staple openings 51 by the staple drivers 64, 66, they pass through the clamped tissue until they impinge upon the recesses 61 on the anvil 46. The inwardly sloped surfaces of the recesses 61 cause the staple legs to bend towards one another to thereby grip the tissue in a manner known in the art.

The housing 54 is dimensioned to removably engage the receiver 42 of the tip 40. To this end, as can be seen in FIG. 9, the distal portion of the housing 54 is provided with two oppositely disposed posts 55 which engage bores or openings 43 in the distal end of the receiver 42 when the cartridge assembly 50 is inserted into the receiver 42. In addition, the anvil 46 is provided with four tissue stop ears 45. As their name implies, tissue stop ears 45 prevent tissue from extending too far into the jaws 42, 46 (i.e., past the most proximal staple openings 51) thereby ensuring that all of the tissue clamped by the jaws 42, 46 is stapled. When the anvil 46 is in the closed position, however, the inner two ears 45 mate with receptacles 63a formed in the upper surface 52 of the shroud 56, and the outer two ears 45 mate with recesses 63b on the sides of shroud 56. The interaction of the ears 45 and the receptacles 63 lock the cartridge assembly 50 in place during firing of the instrument. Finally, the proximal portion of the housing 54 is positioned beneath the pin 48 when the cartridge assembly 50 is disposed in the receiver 42 to further secure the cartridge 50 during use and handling. The engagement of the posts 55 and openings 43, the engagement of the ears 45 and receptacles 63, and the engagement of the housing 54 and the pin 48 can be overcome by opening the jaws 42, 46 and pulling the cartridge assembly 50 distally. Thus, the instrument may be fired repeatedly by replacement of spent cartridges with new ones.

Figure 20:
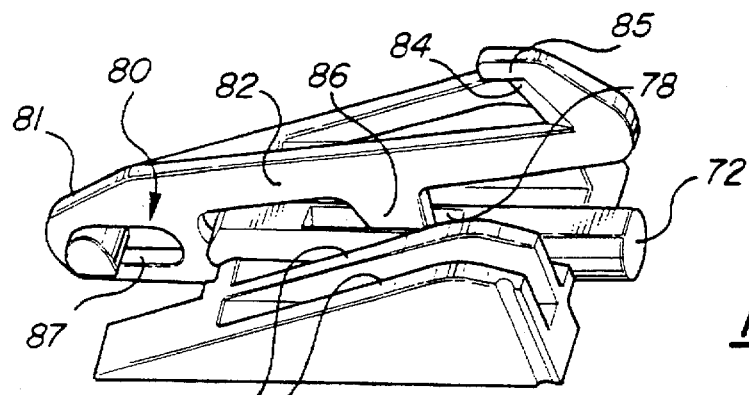
Figure 21:
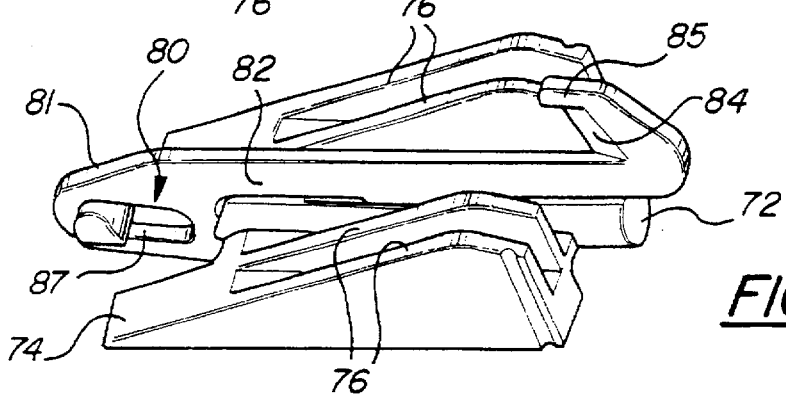

As noted, the preferred embodiment 10 is adapted to divide tissue between the stapled seams shortly after the seams have been formed. To this end, as shown in FIGS. 19-21, the sled 70 is provided with a cutting knife 80 which includes at its proximal end a cutting blade 84. The knife 80 extends through a longitudinal slot 69 formed in the shroud 56 such that blade 84 extends above the upper surface 52 thereof, as shown in FIG. 11. When jaws 42, 46 are in their closed position the extreme upper part of knife 80 extends into slot 41 formed in anvil 46 shown in FIG. 10. Thus, as sled 70 travels distally through the cartridge 50, blade 84 also moves distally between the jaws 42, 46 cutting tissue clamped therebetween.

As shown in FIGS. 19-21, knife 80 is coupled to the sled 70 via a slot 87 in a leg 82 of the knife 80. Slot 87 allows the knife 80 to shift slightly forward (see FIG. 19) relative to the sled 70 and the cartridge 50 when a cartridge 50 is loaded so as to avoid interference between the knife 80 and the pivot pin 48 coupling jaws 42, 46 when a cartridge 50 is loaded. When the instrument 10 is fired, sled 70 initially moves a short distance in the distal direction until it engages the distal end of slot 87 (see FIG. 20). Thereafter, knife 80 will be pulled behind the ramped surfaces 74, 76 of sled 70 at a distance sufficient to ensure that the blade 84 will not divide tissue clamped between jaws 42, 46 until seams have been formed in the vicinity of the blade 84.

Since the blade necessarily is very sharp, the cartridge 50 preferably is designed to minimize risk of injury to persons handling the instrument. For example, as shown in FIG. 9, the shroud 56 of the cartridge 50 preferably is provided with a pair of safety projections 53. The safety projections 53 are disposed one on each side of the proximal end of the slot 69 in shroud 56 through which knife 80 extends. The safety projections 53 are spaced to accommodate passage of the projecting end of knife 80 so that when the knife 80 is in its proximal, unfired position the blade 84 is substantially shielded. Additionally, knife 80 is provided with a radiussed protrusion on overhang 85, as shown in FIG. 16, which extends beyond the blade 84. Thus, projections 53 and overhang 85 reduce the risk that operating personnel will be inadvertently injured when handling a new cartridge 50. Preferably, the instrument 10 is designed to reduce the risk of injury from a spent cartridge as well. Knife 80, therefore, is designed to pivot from a raised cutting position to a retracted position in which it is relatively inaccessible after firing. More particularly, knife 80 is pivotally coupled to sled 70 via the slot 87 at the distal end of knife leg 82. The leg 82 includes a follower 86 which extends through an opening 78 defined in the sled 70, as seen in FIGS. 19-21. Follower 86 rides against a grooved platform 59 disposed on the floor 68 of the cartridge housing 54 (see FIG. 9) as the sled 70 travels distally through the cartridge 50 during firing as illustrated in FIGS. 17-18. As shown in FIG. 16, the distal end of the leg 82 includes a tab 88 that engages the underside of the sled 70. Optionally, tab 88 could be located on the follower 86. Thus, follower 86 and tab 88 cooperate to maintain knife 80 in a raised, cutting position (see FIGS. 11 and 19) as the instrument 10 is fired.

However, as shown in FIG. 9, the grooved platform 59 has a slot 83 near its distal end. When the cartridge 50 is completely fired and the sled 70 nears its distalmost position, the follower 86 falls through the slot 83, the knife 80 pivots downward (see FIG. 21), and the blade 84 falls through the slot 69 and into the central cavity of housing 54. To make sure that the knife 80 pivots into the central cavity, the distal end of the housing 54 is slanted downward and the distal end of the cutting knife 80 includes an angled surface 81 as shown in FIG. 16. The angled surface 81 of the knife 80 contacts the distal end of the housing 54 as the sled 70 completes its distal movement. The cooperation of those slanted surfaces forces the knife 80 to pivot into the housing 54 regardless of the orientation of the tip 40.

Figure 22:
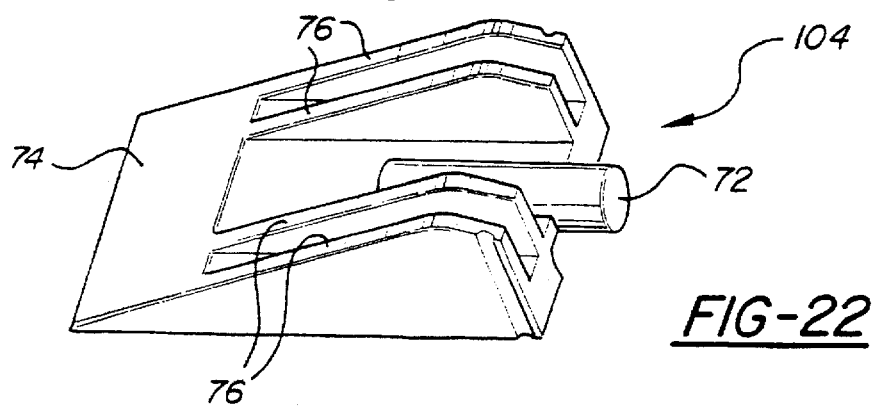
FIG. 22 is a similar perspective view of a first alternate sled 104 suitable for use in the staple cartridge 50 of instrument 10.

While incorporation of a knife is preferred it is not an essential feature of the subject invention. For example, sled 70 may be replaced with an alternate sled 104 shown in FIG. 22. Sled 104 is similar to sled 70 except that it lacks a knife. It has, however, a wide leading camming surface and widely spaced trailing camming surfaces which can drive multiple rows of staple drivers in a manner and with benefits as described above in reference to sled 70.

Figure 23:
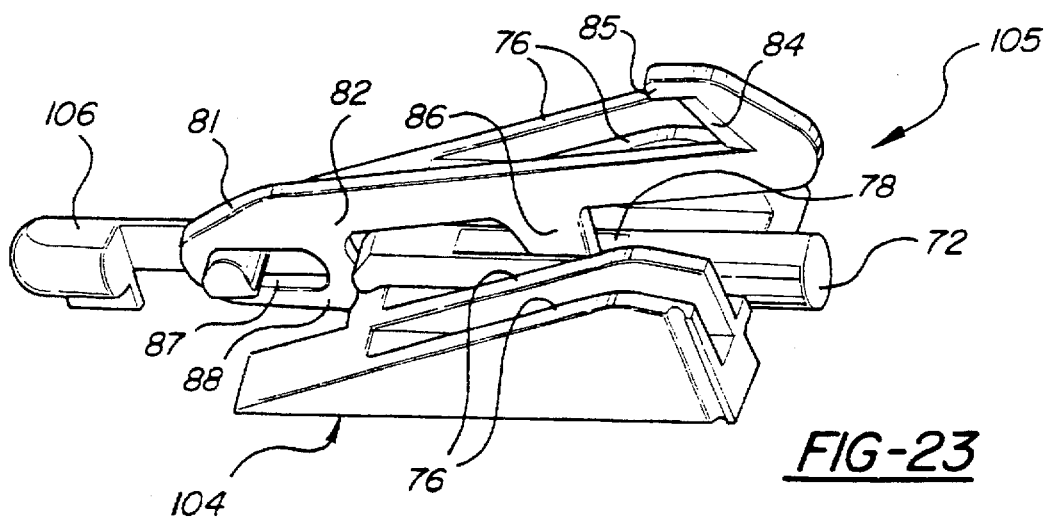
FIG. 23 is a similar perspective view of second alternate sled 105 suitable for use in the staple cartridge 50 of instrument 10.

Sled 70 also can be replaced with another alternate sled 105 shown in FIG. 23. Sled 105 is similar to sled 70 in many respects. However, unlike sled 70, sled 105 includes a visual indicator 106 at its distal end. The cartridge housing 54 may be provided with a suitable opening (not shown) at its distal end so that visual indicator 106 will extend out of the housing 54 when the sled 105 is in its most distal position. The user thus may be provided with a visual indication that a cartridge assembly 50 has already been fired.

The illustrated cartridge assembly 50 is preferred because it allows the surgeon to reliably, efficiently, and easily staple and divide tissue between the jaws. The advantages and features of the illustrated cartridge assembly are described in further detail in an application of Christopher L. Johnson and David A. Dunlap, entitled Linear Stapling Instrument With Improved Staple Cartridge and filed concurrently herewith. The disclosure of that application is hereby incorporated by reference. It will be appreciated, however, that a variety of other cartridge assemblies are known and may be used when linear staplers are constructed in accordance with the subject invention. Obviously, such cartridge assemblies may be omitted entirely when other types or surgical instruments are constructed. The incorporation and specific design of the staple cartridge is not part of the subject invention in its broadest aspects, but rather is a feature of preferred embodiments thereof.

The laparoscopic instrument 10 is provided with a firing system 130 to drive the sled 70 from its proximal, unfired position to its distal, fired position. As shown in FIGS. 27-29, the firing system 130 includes the firing trigger 22 mentioned above, a firing rack 140, a gear train for converting the pivoting movement of the trigger 22 into a longitudinal movement of the rack 140, a firing tube 142, a firing rod 144, and a flexible drive cable 148.

As shown in FIG. 8, the trigger 22 is pivotally mounted upon a spindle 131 formed on the interior of the handle 20. It is biased towards its unfired position by one or both of a preloaded torsion spring 132 and an extension spring 138, as shown in FIGS. 33-36. A fixed arm 132b of the torsion spring 132 engages an extension of the interior wall of handle 20. The free arm 132a engages the end of a wall 139 located in the interior of trigger 22. The extension spring 138 extends between suitable posts near the bottom of the grip of handle 20 and on the trigger 22. Thus, in order to squeeze the trigger 22, a user must overcome the force of the torsion spring 132 and the extension spring 138, and once the firing stroke is completed, the trigger 22 automatically will return to its initial, unfired position.

Preferably, trigger 22 is provided with a feel which is comfortable to a surgeon. The force required to drive sled 70 as the cartridge 50 is fired obviously will contribute significantly to the feel of the trigger 22, and toward that purpose the firing force of cartridge 50 provides a favorable force profile. Consequently, the design of the trigger 22, torsion spring 132, and extension spring 138 preferably is coordinated to provide relatively uniform resistance across the entire stroke of the trigger 22.

It will be appreciated, therefore, that the trigger wall 139 when the trigger 22 is in its initial, unfired position, contacts the torsion spring 132 at a point well below the tip of spring arm 132a (see FIG. 33). Trigger 22 and spring arm 132a also pivot in opposite directions on separate pivot axes as the trigger 22 is operated. Consequently, as trigger 22 is pivoted inwardly from its initial position to commence firing, the contact point between trigger wall 139 and torsion spring 132 moves radially outward along spring arm 132a (see FIG. 36), and pivoting of the trigger 22 imparts decreasing movement to spring arm 132a. Those effects offset the increasing force required to move spring arm 132a.

Near the end of its stroke, however, continued pivoting of the trigger 22 imparts very little movement to the spring arm 132a. In this range of movement, therefore, torsion spring 132 offers very little resistance to pivoting of the trigger 22. Extension spring 138, however, offers increasing resistance as trigger 22 continues to pivot. That tends to compliment the decreasing resistance or torsion spring 132 near the end of the trigger stroke, and the overall effect is to provide more uniform resistance throughout the entire stroke of the trigger 22.

The trigger 22 includes a pair of integrally formed arcuate gear racks 134. The rotation of the trigger 22 about the spindle 131 causes a similar rotational movement of the arcuate gear racks 134. As best appreciated from FIGS. 8 and 33-36, the arcuate gear racks 134 mesh with two pairs of gear teeth 133 which are attached to a gear 137. The compound gear assembly 135 of gears 133, 137 is pivotally mounted on another spindle 136 formed on the interior of the handle 20 such that gear teeth 137 mesh with the rack 140. Thus, when a user squeezes the trigger 22 towards the handle 20, the arcuate gears 134 cause the compound gear 135 to rotate which, in turn, drives the rack 140 distally thereby converting the rotational or pivoting movement of the trigger 22 into longitudinal movement of the rack or driver 140.

As illustrated in FIGS. 27 and 33-36, the distal end of the rack or driver 140 is rotatably coupled to the proximal end of the firing tube 142. More specifically, driver 140 is an elongated, substantially cylindrically-shaped tube which includes an annular trough 141 disposed about the outer circumference of its distal end. Likewise, firing tube 142 is an elongated, substantially cylindrically-shaped tube. The proximal end of the firing tube 142 includes a pair of opposed tabs 143. Tabs 143 angle slightly inward such that they snap into and mate with the trough 141 on the driver 140 to secure the firing tube 142 and the driver 140 together while permitting relative rotation between these two components. This arrangement permits the driver 140 to transfer its longitudinal motion to the firing tube 142 while simultaneously permitting relative rotation between the components of the firing system 130 disposed in the shaft 30 and the components disposed in the handle 20. Thus, the firing system 130 is adapted to accommodate rotation or the shaft 30 relative to the handle 20.

The rack 140 and firing tube 142 preferably are an elongated, substantially cylindrically-shaped rod and tube, respectively, as shown. When configured in such a manner, as will become apparent from the description of the jaw closure and articulation control systems which follows, they may accommodate and be accommodated within tubular components of other mechanical systems in the instrument 10. Further, since the shaft tube 31 is an elongated, substantially cylindrically-shaped tube, by configuring the rack 140 and tube 142 in a like manner space within the shaft tube 31 is more efficiently utilized. Moreover, since their essential function is that of a reciprocating drive shaft, by situating them more or less concentrically to the longitudinal axis of the shaft 30, they transmit force with less of a moment which otherwise might tend to bend the shaft.

The distal end of the firing tube 142 is fixedly attached to the proximal end of the firing rod 144 as shown in FIG. 27. This firing rod 144 is rigid, and thus, longitudinal movements of the firing tube 142 are reflected in corresponding movements of the firing rod 144.

The distal end of the firing rod 144 is fixedly attached to the flexible cable 148. The flexible cable 148 extends from the distal end of the driver rod 144, through the articulation joint, into the tip 40 of the instrument 10, and ultimately abuts against the sled 70. Thus, distal motion of the cable 148 drives the sled 70 distally through the cartridge 50 firing the cartridge 50 as described above. Moreover, since the cable 148 is flexible and can bend at the articulation joint, the instrument 10 may be fired when the tip is articulated.

Since cable 148 is flexible, the shaft 30 and tip 40 assemblies preferably provide lateral support for the cable 148 to prevent it from buckling and to more efficiently and reliably transmit force from the firing rod 144 to the sled 70. Accordingly, as shown in FIGS. 27–29, the flexible cable 148 passes through a groove which extends along the bottom of a U-shaped channel in the insert 33 carried in clevis body 32. The groove closely accommodates cable 148, and the channel of insert 33 accommodates a camming driver 94 (described in further detail below in connection with the jaw closure system 89) over the groove. The insert 33 extends longitudinally close to, and the camming driver 94 extends beyond the articulation axis. Thus, cable 148 is laterally constrained within the groove and bending of the cable 148 within the shaft 30 is minimized.

Similarly, the tip 40 includes a receiver insert 108, as shown in FIGS. 28–29, which is disposed near the proximal end of receiver 42 between the cartridge 50 and the articulation joint. The cable 148 passes through a bore in the receiver insert 108. The cable 148 then passes through a bore in the cartridge shroud 56 and into the groove in platform 59 of cartridge floor 68 (see FIG. 9). Those bores and grooves are sized to closely accommodate the flexible cable 148, thereby laterally constraining it and minimizing flexing of the cable 148 in the tip 40.

As best appreciated by comparing FIGS. 28–29, the camming driver 94, when it is in its distal, clamping position, extends from the distal end of the clevis body insert 33, through the articulation joint, and onto the top surface of the proximal end of the receiver insert 108. The proximal end of the receiver 42 extends through the articulation joint and under the lower surface of clevis body insert 33. The cable 148 passes therebetween, and thus, it will be appreciated that it is substantially constrained from bending out of the plane of articulation.

Necessarily, however, the cable 148 must bend in the plane of articulation when the tip 40 is articulated. Such bending invariably increases to some degree the tendency of a cable to buckle, the resistance of a cable to movement through the articulation joint, and the tendency of the tip to straighten when force is transmitted through the cable. Accordingly, in instrument 10 cable 148 passes through a flexible guide 145 which extends generally between the clevis body insert 33 in shaft 30 and the receiver insert 108 on receiver 42.

The proximal portion 145a of guide 145, as best seen in FIG. 28, is elongated and has a generally U-shaped cross-section with lips extending perpendicular from the sidewalls thereof. The proximal portion 145a of the guide 145 is accommodated in the distal end of the groove in clevis body insert 33. The groove has adjoining recesses which accommodate the side lips of guide 145 such that the upper surface thereof is flush with the surface of the clevis body insert 33. A pair of arms 145b extend from the sides of the proximal portion 145a of the guide 145 distally through the articulation joint. The arms 145b terminate in hooks 145c which are received in a shallow, rectilinear well 109 in receiver 42.

The arms 145b are relatively thin, elongated rectilinear members having a length which extends in the plane of articulation and a width which extends perpendicular thereto. The width of the arms 145b is large relative to the diameter of the cable 148, preferably at least as wide as the cable diameter. Thus, the arms 145b are flexible and provide support for the cable when the tip 40 is articulated. In accordance therewith, the arms 145b, when the tip is in its aligned or unarticulated position, are adjacent to the cable 148 to minimize any play in the cable 148 which otherwise might exist.

Furthermore, the length of well 109 in receiver 42 are oversized relative to arm hooks 145c. As the instrument 10 articulates, therefore, hooks 145c can slide longitudinally within well 109, thereby allowing the guide arms 145b to bend, each independently of the other, in a concentric fashion. Thus, binding of the cable between the arms 145b is avoided. Preferably, the well 109 is sized so that, when the tip 40 is fully articulated, the hook 145c of the guide arm 145b having the larger radius engages the proximal end of well 109 to impart to the arm 145b a uniform bend which is inscribed by the angle of articulation. In this manner, the arms 145b will provide rigid support for the cable 148 over a like bend and will preclude any buckling of the cable 148 in the plane of articulation.

It will be appreciated, of course, that since the ends of the guide arms 145b are slidably engaged with receiver 42, that the arms 145b may not prevent all buckling of cable 148. When the tip is less than fully articulated, the arms 145b may slide and permit cable 148 to buckle somewhat until the hooks 145c engage the proximal end of well 109. At the same time, however, it will be appreciated that the arms 145b allow progressively less buckling of cable 148 as it is increasingly articulated and, thus, is increasingly susceptible to buckling.

It also will be appreciated, therefore, that the guide 145 serves to impart a more uniform bend to cable 148 as the tip 40 is articulated. The guide 145 also provides a smooth surface over which cable 148 may travel in passing out of the shaft 30 and into the tip 40. Thus, the guide 145 helps to reduce the resistance of cable 148 to movement through the articulation joint, and correspondingly, reduces the force required to fire the instrument 10. The guide 145 also helps to inscribe the bending of cable 148 within the angle of articulation. To the extent that is accomplished, the guide 145 helps to minimize moments which tend to move the tip 40 when the instrument 10 is fired in an articulated position.

As noted above, cable 148 abuts sled 70 when the sled 70 is in its proximalmost, loaded position. More precisely, cable 148 abuts sled 70 on a proximally facing bearing surface 72. Thus, when a user squeezes trigger 22, thereby driving cable 148 forward, cable 148 will drive the sled 70 distally through the cartridge 50. The cable 148, however, is not hooked or otherwise attached to the sled 70. Consequently, when trigger 22 is released and the firing system 130, including cable 148, returns to its unfired position, sled 70 remains in its distalmost position and, more importantly, knife 80 remains in its retracted position. If a user attempts to refire a previously fired cartridge, therefore, the knife 80 is incapable of severing unstapled tissue.

The illustrated firing system 130 is preferred because it allows a surgeon to reliably, efficiently, and easily fire the cartridge 50. The advantages and features of the illustrated firing system 130 are described in further detail in an application of Jeffrey R. Oberlin Christopher L. Johnson, and David A. Dunlap, entitled Articulated Surgical Instrument with Improved Firing Mechanism and filed concurrently herewith. The disclosure of that application is hereby incorporated by reference. It will be appreciated, however, that a variety of firing systems are known and may be used when linear staplers are constructed in accordance with the subject inventions. Different types of firing systems also will be used when other types of instruments, such as hernia staplers and clip appliers, are constructed in accordance with the subject invention. The specific design of the firing system is not part of the subject invention in its broadest aspects, but rather is a feature of preferred embodiments thereof.

Figure 24:
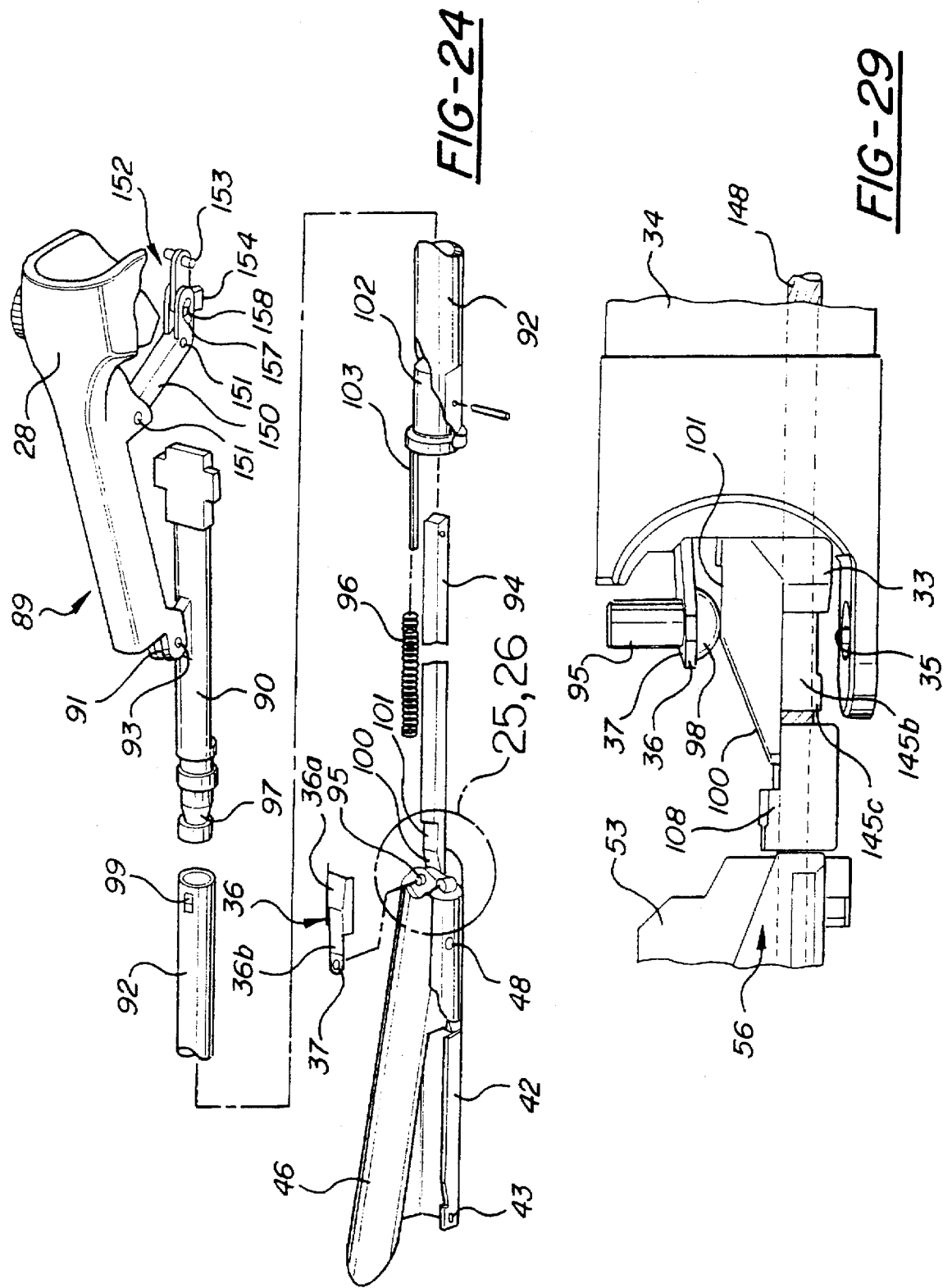
FIG. 24 is a partially exploded, top perspective view of the jaw closure system 89 and selected other components of instrument 10.
Figure 25:
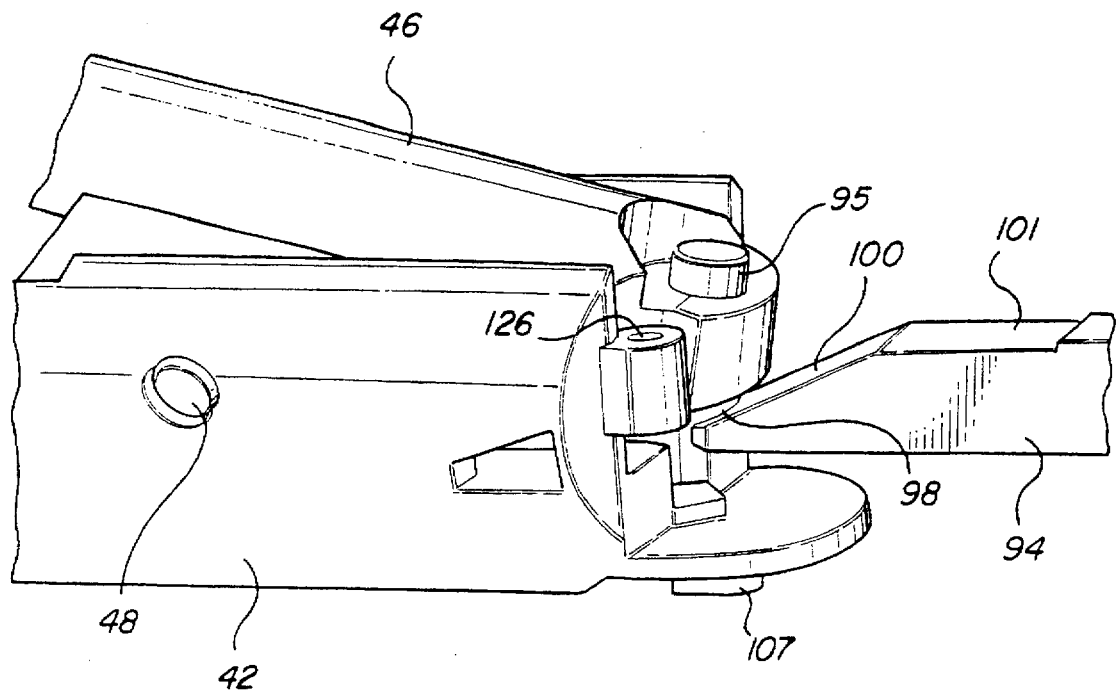
FIG. 25 is a top, left side perspective, partial view of the camming driver 94 and tip assembly 40 of instrument 10, showing camming driver 94 in the open jaw position.
Figure 26:
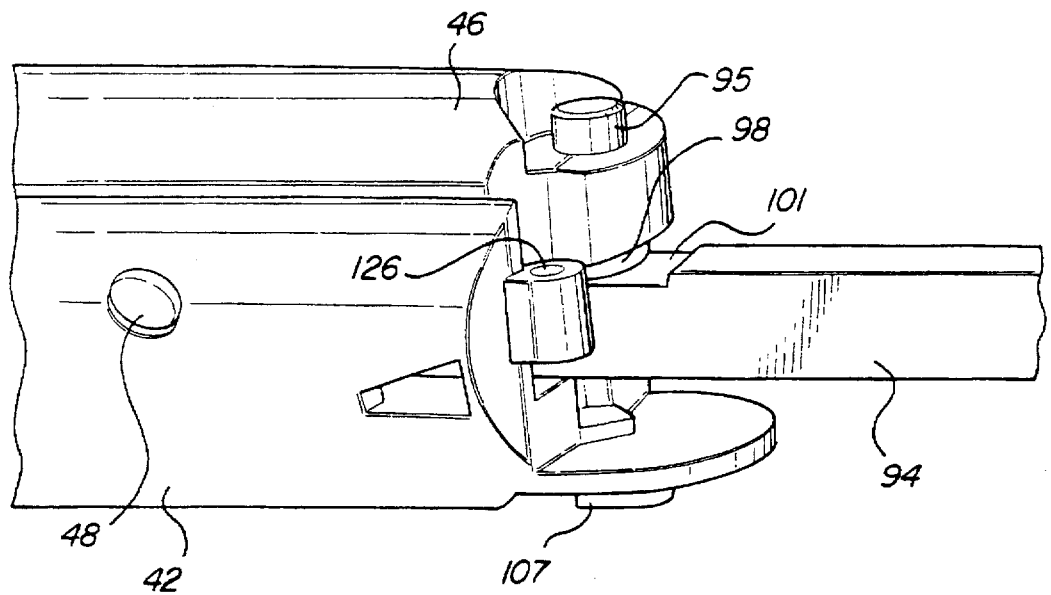
FIG. 26 is a view similar to FIG. 25 showing camming driver 94 in the closed jaw position.

In order to move the jaws 42, 46 between the open and closed positions, the instrument 10 is provided with a clamp-up or jaw closure system 89 as illustrated in FIGS. 24–26. More particularly, the jaw closure system 89 biases the anvil 46 in its open position and enables the anvil 46 to be moved into a closed position and held there. This jaw closure system 89 includes the clamp-up lever 28 mentioned above; a clamp-up driver 90; a clamp-up tube 92; the camming driver 94 mentioned above; a return spring 96; leaf spring 36 mentioned above, and a cam projection 98.

As illustrated in FIGS. 24 and 33–36, the clamp-up lever 28 is pivotally coupled to the clamp-up driver 90 via a pin 93 which extends through bores in a pair of arms 91 extending from its distal end. The proximal end of the clamp-up lever 28 is secured to the handle 20 via link 150. Link 150 is pivotally coupled to both the clamp-up lever 28 and to the handle 20 by pins 151. The clamp-up tube 90 is disposed in the handle 20 for reciprocating, longitudinal movement between a proximal position and a distal position. As a result, when the clamp-up lever 28 is moved from the raised, open position illustrated in FIG. 2 to the lowered, closed position illustrated in FIG. 3, the clamp-up driver 90 is driven from its proximal position to its distal position. In other words, this arrangement translates the downward pivoting motion of the lever 28 into distal movement of the driver 90, as may be appreciated by comparing FIGS. 34 and 35.

The jaw closure system 89 is adapted to accommodate rotation of the shaft 30 relative to the handle 20. To this end, the distal end of the driver 90 is rotatably coupled to the proximal end of the clamp-up tube 92, as best appreciated from FIGS. 24 and 33–36. As in the firing system 130, this rotatable engagement is implemented by providing an annular trough 97 in the outer surface of the substantially cylindrical distal end of the driver 90 and a pair of opposed tabs 99 formed in the proximal end of the clamp-up tube 92. The trough 97 and tabs 99 secure the clamp-up tube 92 and the driver 90 together while permitting relative rotation between these two components. This arrangement permits the driver 90 to transfer its longitudinal motion to the clamp-up tube 92, and vice versa, while simultaneously permitting relative rotation between the portions of the jaw closure system 89 disposed in the shaft 30 and the portions disposed in the handle 20.

As shown in FIG. 24, the clamp-up tube 92 is coupled to the camming driver 94 via a plug 102. The longitudinal movements of the tube 92, therefore, are transmitted to the camming driver 94 through this direct connection.

As shown in FIG. 27, camming driver 94 is an elongated rod having a substantially rectangular cross section. Camming driver 94 is disposed in the elongated insert 33 carried in clevis 32 disposed at the distal end of shaft assembly 30. More particularly, camming driver 94 can slide within a closely-fitting, U-shaped channel extending the length of clevis body insert 33.

In order to control the movements of the camming driver 94, the return spring 96 is positioned, preferably in a preloaded state, around pin 103 on the plug 102 which extends into a receiving pocket in the clevis body 32 (see FIG. 30). Distal movements of the clamp-up tube 92 compress spring 96 between the plug 102 and the clevis body 32. Accordingly, spring 96 biases camming driver 94 towards its proximal position and the clamp-up lever 28 toward its open position. The return spring 96 also will assist the camming driver 94, the clamp-up tube 92, the clamp-up driver 90, and the clamp-up lever 28 in their return movements when the jaws 42, 46 are to be released from the clamped position.

Leaf spring 36 is mounted at the distal end of shaft assembly 30 between the distal end of clevis body 32 and the shaft end piece 34. As previously noted, anvil 46 is coupled to leaf spring 36 to permit articulation of tip 40 relative to shaft 30. It will be appreciated, however, that leaf spring 36 also serves to bias anvil 46 in its open position.

As most easily seen in the magnified views depicted in FIGS. 25 and 26, the distal end of the camming driver 94 forms a camming surface 100. Pin 95, which as noted above couples anvil 46 to leaf spring 36, also provides anvil 46 with a camming projection 98 on the underside of anvil 46 proximal to jaw pivot pin 48. The camming surface 100 of camming driver 94 and the camming projection 98 interact to pivot the anvil 46 relative to the receiver 42 and thereby to close the jaws 42, 46.

More specifically, when the camming driver 94 is driven distally from its proximal position by the pivoting of the lever 28 from the open to the closed positions and the subsequent distal movements of the driver 90 and the clamp-up tube 92, the camming surface 100 rides under the cam projection 98 as will be seen by comparing FIGS. 25 and 26. This movement of the camming driver 94 effectively lifts both the cam projection 98 and the proximal end of the anvil 46. Since cam projection 98 is situated proximal to jaw pivot pin 48, lifting of the cam projection 98 causes anvil 46 to pivot downward about pin 48 toward its closed position. When the jaws 42, 46 are positioned around body tissue, the pivoting of the anvil 46 firmly clamps the tissue between the surface 49 of anvil 46 and the upper surface 52 of the cartridge assembly 50 carried by the receiver 42.

The cam projection 98 on anvil 46 is a hemispherically-shaped projection and camming surface 100 on camming driver 94 is a planar ramped surface. Consequently, the hemispherical cam projection 98 and the planar ramped surface 100 define a mechanical point at which the contact and camming occurs. Because there is such a camming point, tip 40 may be articulated relative to the shaft 30 and to the camming driver 94. It is not necessary that the camming point be a point in the mathematical sense, but it will be appreciated that as the size of the camming contact area increases, articulation of the tip 40 will generate increasing torque in the jaws 42, 46 which will tend to cause them to twist out of the intended plane of articulation. Resistance to articulation likewise will be increased, and eventually, this torque will preclude any articulation of the jaws.

The center of hemispherically-shaped projection 98 (i.e. the center of the imaginary sphere corresponding thereto) is located proximate to the articulation axis of the instrument 10. More specifically, as best appreciated by viewing anvil 46 in its closed position shown in FIGS. 26 and 29, the center of projection 98 is located on the axis which extends through bores 47, 37, 35, pin 95, and post 107. Consequently, when tip 40 is articulated, cam projection 98 will rotate, but it will not translate relative to camming surface 100. Further, the curved surface of protection 98 has an axis of symmetry which is proximate to the articulation axis. This ensures that movement of the anvil 46 in response to movement of the camming driver 94 is the same regardless of the angle to which the tip 40 is articulated.

It also will be appreciated that by situating the center of hemispherically-shaped cam projection 98 on the articulation axis the cam point between cam projection 98 and camming surface 100 will be proximate to the articulation axis. Consequently, there is no need to transfer the clamping force of the camming driver "around a corner" when the tip is in an articulated position. The cam point need not be situated exactly on the articulation axis, but it will be appreciated that as it becomes more remote therefrom distal movement of the camming driver 94 when tip 40 is articulated will tend to cause further articulation of the tip 40 beyond its intended position. The camming driver 94 also will tend to cause twisting of the anvil 46 relative to the plane of articulation, and this torque can create some resistance to closing of the anvil 46.

Consequently, the hemispherically-shaped cam projection 98 and the planar ramped camming surface 100 provide efficient and predictable closure of the jaws 42, 46 regardless of the degree to which the tip 40 is articulated. The mechanical efficiency of that operation obviously can be varied or staged by changing the slope of camming surface 100.

In order to insure that jaws 42, 46 remain in the clamped or closed position despite the counteracting forces generated by the anvil leaf spring 36, the return spring 96, and any elasticity in the tissue clamped between the jaws 42, 46, the ramped surface 100 of the camming driver 94 terminates in a flat surface 101, as shown in FIGS. 25 and 26. Thus, after cam projection 98 has traversed the length of camming surface 100 it will come to rest on flat 101. The intersection between camming surface 100 and flat 101 may be radiussed slightly to allow easier movement of cam projection 98 over the intersection, especially when the jaws 42, 46 are being clamped over relatively thick tissue.

At this point, leaf spring 36 and the elasticity of clamped tissue generate sufficient friction between the cam projection 98 and flat 101 to counteract the force generated by spring 96. Consistent with that purpose, flat 101 is sufficiently parallel to the reciprocating movement of camming driver 94 so that cam projection 98 will remain thereon. At the same time, however, flat 101 may be angled slightly downward toward the distal end of the camming driver 94 so that the camming driver 94 may be moved off flat 101 more easily when the jaws 42, 46 are unclamped. It is believed an angle on the order of 5° will suffice for such purposes.

Thus, under normal circumstances, once the jaws 42, 46 are clamped over tissue the cam projection 98 will remain on flat 101, and camming driver 94 will remain in its distal, clamped position, until the camming driver 94 is manually moved proximally by lifting the clamp-up lever 28 from its lowered, clamped position. As a result, once the jaws 42, 46 are moved to the clamped position illustrated in FIG. 26, they will preferably remain in such position until a surgeon desires to open the jaws 42, 46.

The illustrated jaw closure system 89 is preferred because it allows a surgeon to reliably, efficiently, and easily control the operation of the jaws of the instrument. The advantages and features of the illustrated jaw closure system are described in further detail in an application of Hugh Melling, Christopher L. Johnson, and Jeffrey R. Oberlin, entitled Articulated Surgical Instrument With Improved Jaw Closure Mechanism and filed concurrently herewith. The disclosure of that application is hereby incorporated by reference. It will be appreciated, however, that a variety of other jaw closure systems are known and may be used when linear staplers and other surgical instruments having a pair of opposed, pivoting jaws are constructed in accordance with the subject invention. Likewise, other instruments within the scope of the subject invention may not utilize a pair of opposing jaws, and in such instruments there is no need for a jaw closure system. The incorporation and specific design of the jaw closure system is not part of the subject invention in its broader aspects.

Figure 32:
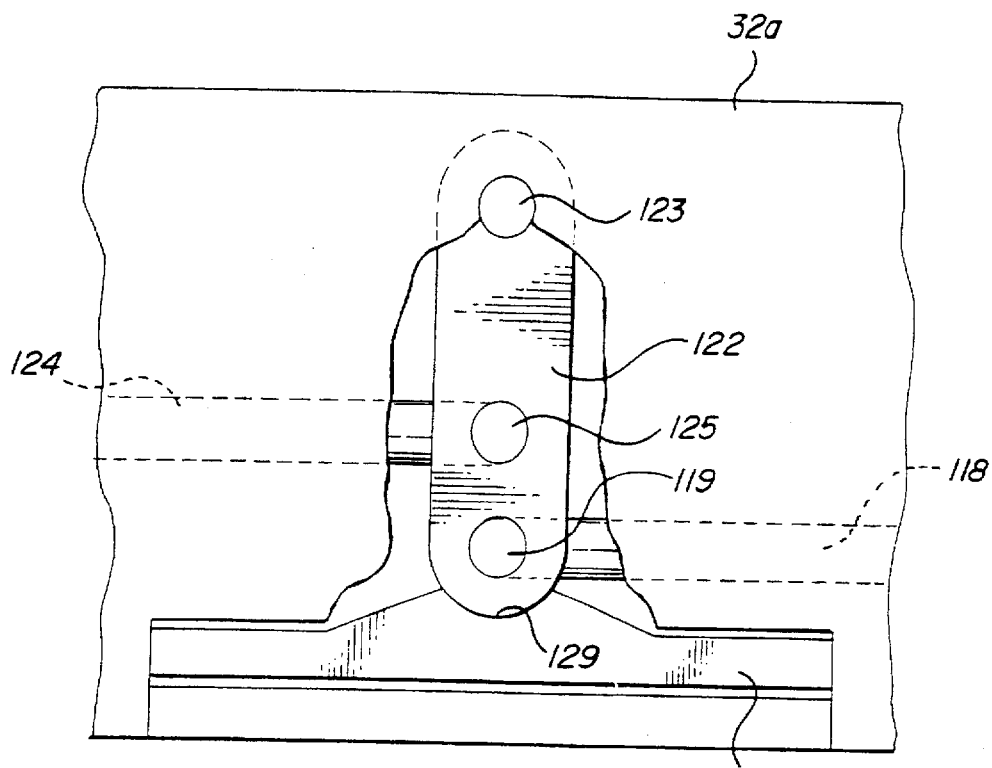
FIG. 32 is a left side elevational, partial view of shaft clevis half 32a, a portion thereof being torn away to show certain components of the articulation control system 110.

In order to provide control over the articulation of the tip 40, the instrument 10 is provided with an articulation control system 110 as illustrated in FIGS. 30–32. The articulation control system 110 includes the articulation slide control 26 mentioned above; an articulation driver 112; an articulation tube 116; a proximal rod 118; a desensitizing link 122; and a distal rod 124.

As discussed above, the articulation slide control 26 is associated with the handle 20 and can be manipulated by a surgeon to articulate the tip 40 to a desired position. To this end, and referring to FIG. 8, the articulation slide control 26 includes oppositely disposed, inwardly projecting longitudinal ribs 13 which engage longitudinal grooves 14 defined in the exterior surface of handle halves 25, 27. Thus, the slide control 26 is adapted for reciprocating longitudinal movement between a distal position and a proximal position.

Moving the slide control 26 forward will cause the tip 40 to articulate to the right as illustrated in FIG. 31. Moving the slide control 26 rearward will cause the tip 40 to articulate to the left (not shown). (Of course, if the shaft 30 is rotated 180° from the position illustrated in FIGS. 22 and 23 such that the receiver 42 is disposed above the anvil 46 these directions will be reversed so that forward movement of the slide control 26 will pivot the tip 40 to the left and vice versa).

As shown FIGS. 30 and 31, the distal end of the shaft 30 assembly is beveled on opposing sides to permit the jaws to articulate a full 45° in either direction. By providing the instrument 10 with the ability to articulate a full 45° in either direction from the aligned, neutral position, a surgeon can manipulate the instrument to reach more tissue areas more easily. Greater or lesser ranges or articulation may be provided, however. Likewise, the tip, may be designed to articulate in a single direction if desired.

As illustrated in FIGS. 30 and 31, the articulation slide control 26 is directly connected to the articulation driver 112. Thus, movements of the slide control 26 are directly reflected in corresponding movements of the driver 112.

As in the firing system 130 and the jaw closure system 89 described above, the articulation control system 110 is adapted to accommodate rotation of the shaft 30 relative to the handle 20. To this end, the distal end of the articulation driver 112 is rotatably coupled to the proximal end of the articulation tube 116, as can be seen in FIGS. 30 and 33–36. As in the firing and jaw closure systems 130, 89, this rotatable engagement is implemented by providing an annular trough 113 in the outer surface of the substantially cylindrical distal end of the articulation driver 112 and a pair of opposed tabs 114 formed in the proximal end of the articulation tube 116, as shown in FIG. 30. The trough 113 and tabs 114 secure the articulation tube 116 and the driver 112 together while permitting relative rotation between these two components. This arrangement permits the driver 112 to transfer the longitudinal motion of the articulation control 26 to the articulation tube 116 while simultaneously permitting relative rotation between the portions of the articulation control system 110 disposed in the shaft 30 and the portions disposed in the handle 20.

The articulation tube 116 is coupled to the proximal rod 118 as shown in FIGS. 30 and 31. Thus, longitudinal movements of the articulation tube 116 cause corresponding movements in the proximal rod 118. These same movements are transferred to the distal rod 124. However, in order to attenuate the movement of the distal rod 124 relative to the movement of the proximal rod 118, and ultimately to attenuate the articulation of tip 40 relative to the sliding of control 26, the two rods 118, 124 are coupled through the desensitization link 122.

More particularly, as shown in FIGS. 30–31, proximal rod 118 is an elongated, relatively narrow, cylindrically-shaped rod extending generally through the shaft assembly 30 near its distal end. The proximal end of proximal rod 118 is pivotally coupled to the articulation tube 116. Thus, reciprocating longitudinal movements of the articulation tube 116 cause corresponding movements in the proximal rod 118.

Desensitizing link 122 of the preferred embodiment 10 is pivotally coupled to the clevis half 32a mounted near the distal end of shaft assembly 30. More precisely, as shown in FIG. 32, desensitizing link 122 is pivotally attached to clevis half 32a at pivot point 123 such that it can rotate about pivot point 123 in both directions. The distal end of proximal rod 118 is pivotally coupled to the desensitizing link 122 at pivot point 119. Accordingly, proximal rod 118 causes desensitizing link 122 to rotate as it reciprocates between its proximal and distal positions.

Distal rod 124, which is configured similarly to proximal rod 118 extends generally through the shaft assembly 30 at its distal end. The proximal end of distal rod 124 is pivotally coupled to the desensitizing link 122 at pivot point 125. Rotation of the desensitizing link 122, therefore, causes distal rod 124 to reciprocate longitudinally within the shaft 30.

Distal rod 124 is coupled at its distal end to a bore 126 positioned near the proximal end of the receiver 42. As shown in FIGS. 30 and 31, the bore 126 is positioned near the left side of the receiver 42. As a result, distal movements of the distal rod 124 will apply a pushing force to the left side of the receiver 42 thereby causing the tip 40 to articulate or pivot to the right (to an observer looking down the shaft 30 when the receiver 42 is positioned beneath the anvil 46 as shown in FIG. 23). Conversely, proximal movements of the distal rod 124 will apply an off center pulling force to the receiver 42 thereby causing the tip 40 to articulate in the opposite direction.

Desensitization link 122, as best seen in FIG. 32, is an elongated arm-like structure. The pivot 123 connection to clevis half 32a is at one end of the link 122 and the pivot 119 connection to the proximal rod 118 is at the other end of link 122. The pivot 125 connection to the distal rod 124 is in the middle of link 122. More to the point, the distance between the distal rod pivot point 125 and the link pivot point 123 is less than the distance between the proximal rod pivot point 119 and the link pivot point 123. Movement of the distal rod 124, therefore, will be attenuated relative to movement of proximal rod 118. Moreover, because movement of the distal rod 124 is attenuated by desensitization link 122, articulation of the tip 40 relative to movement of slide 26 will be attenuated as well.

As will be appreciated from the discussion of the firing system 130 above, the flexible cable 148 and flexible guide 145 create some increasing resistance to the articulation of tip 40 as the degree of articulation increases Although this resistance to articulation is relatively low, a surgeon generally will prefer a uniform feel to an instrument. The fact that articulation of the instrument is met with increasing resistance could be discomforting. Accordingly, the articulation control system preferably is designed to offset this effect.

To that end, therefore, in the preferred embodiment 10, for example, pivot point 123 is fixed proximate to an imaginary line (not shown) extending between the point where proximal rod 118 connects to articulation tube 116 and the point where distal rod 124 connects to receiver 42. Consequently, when desensitizing link 122 is in its neutral, "unarticulated" position (shown in FIG. 30), it bends proximal rod 118 and distal rod 124 out of the positions they normally would occupy. As rods 118, 124 are moved distally or proximally to articulate the tip 40 (shown in FIG. 31), therefore, the stress in rods 118, 124 is relieved, and rods 118, 124 urge the tip 40 towards an articulated position. The articulating force thus generated tends to offset the increasing resistance of the tip 40 to articulation which is caused by flexing of the firing system.

The firing system of an articulated instrument, since it necessarily must transfer force around a corner, also can create a moment which may cause the tip to straighten or otherwise move when the instrument is fired in an articulated position. The firing system 130 of the illustrated instrument 10, as discussed above, is designed to minimize such moments and any resulting movement. Preferably, however, the articulation control system also is designed to minimize movement of the tip when the instrument is fired in an articulated position.

Figure 8A:
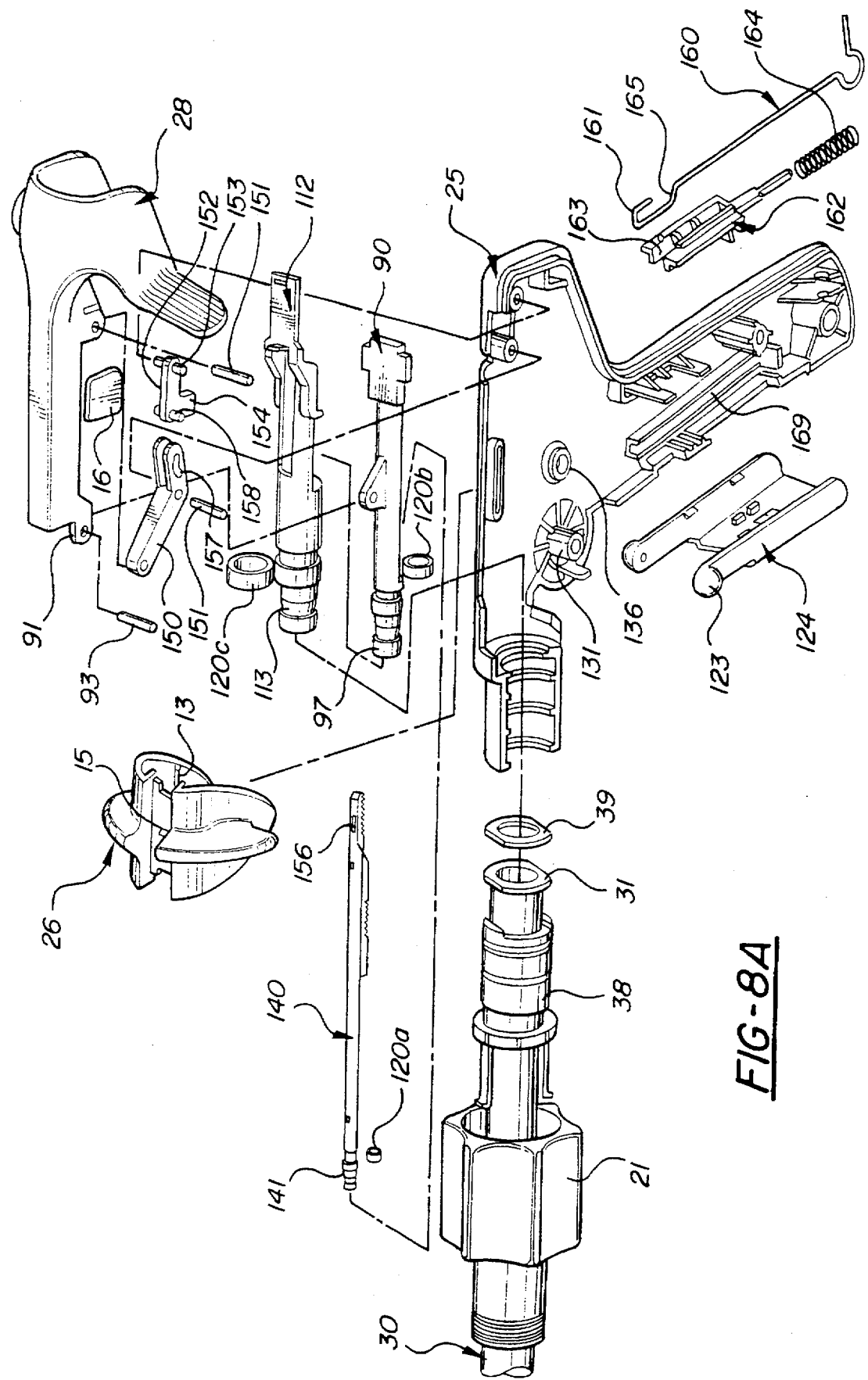

For example, as shown in FIG. 8A, the slide control 26 of the instrument 10 has a tooth 15 upstanding from an upper surface thereof. The clamp-up lever 28 has an elastic body 16 which is composed of a natural or synthetic rubber or of another elastomeric material. The elastic body 16 is disposed in a cavity provided on the undersurface of the clamp-up lever 28 for such purposes. As best appreciated from FIGS. 33–36, when the clamp-up lever 28 is closed, the tooth 15 bites into the elastic body 15, thereby immobilizing the articulation slide control 26. Consequently, the tip 40 cannot be articulated when the jaws 42, 46 are closed, but more importantly, the tip 40 is stabilized and resistant to any firing forces which otherwise would tend to cause the tip 40 to move.

Since the instrument 10 cannot be inserted through a cannula when it is articulated, the articulation control system preferably is designed so that the tip 40 may be located easily and reliably in the unarticulated position. For example, as will be appreciated from FIG. 32, clevis half 32a, to which desensitizing link 122 is mounted, has an integral leaf spring portion 128 which extends under desensitization link 122. Leaf spring 128 has a shouldered detent 129 into and out of which the end of desensitization link 122 may pivot. Flexing of leaf spring 128 allows desensitization link 122 to pivot into and out of engagement with detent 129 more easily. Thus, the interaction between the detent 129 and the end of desensitization link 122 provides a surgeon with tactile feedback concerning the position of the tip 40 and also helps prevent the tip 40 from being inadvertently moved from its centered position relative to the shaft 30 during use and handling.

It should be noted that, when the jaw closure system 89, the articulation control system 110, and the firing system 130 are all incorporated into the same instrument 10, the clamp-up driver 90, the clamp-up tube 92, the articulation driver 112, the articulation tube 116, the firing rack 140, and the firing tube 142 preferably all are elongated, substantially cylindrically-shaped tubes or rods which are more or less concentrically disposed relative to the shaft 30 as shown. More particularly, the clamp-up driver 90 and the clamp-up tube 92 are preferably chosen to fit within the articulation driver 112 and the articulation tube 116, respectively, and the firing rack 140 and the firing tube 142 are chosen to fit within the clamp-up driver 90 and the clamp-up tube 92, respectively, as shown in FIGS. 33–36. The bottom half of the proximal portion of clamp-up driver 90 and articulation driver 112 is cut away to allow the compound gear 135 to pass therethrough and engage the firing rack 140. Similarly, an opening is provided in the upper portion of the articulated driver 112 so that lever 28 can be coupled to clamp-up driver 90.

Thus, not only is space within the instrument efficiently utilized, but the shaft 30 assembly may be easily sealed to prevent the passage of gas and body fluids. For example, as shown in FIG. 8, elastic annular seals 120a, 120b, and 120c are disposed around, respectively, firing rack 140, clamp-up driver 90, and articulation driver 112 in annular seats provided therein. A silicone or other type of sealant/lubricant may be added in this area. Other methods of sealing the shaft are known, however, and may be used if desired.

The illustrated articulation control system 110 is preferred because it allows the surgeon to reliably, efficiently, and easily control articulation of the operating tip of the instrument. The advantages and features of the illustrated articulation control system are described in further detail in an application of Jeffrey R. Oberlin and Mark A. Penrod, entitled Articulated Surgical Instrument With Improved Articulation Control Mechanism and filed concurrently herewith. The disclosure of that application is hereby incorporated by reference. It will be appreciated, however, that the manner in which articulation of the operating tip is controlled is not part of the subject invention.

The subject invention encompasses instruments which have an operating mechanism and a control mechanism. The operating mechanism is used to perform a surgical procedure, that is, it is a mechanism which actually accomplishes the surgical procedure, such as cutting, stapling, grasping, and the like, for which the instrument is designed. The control mechanism is used to move, immobilize or otherwise manipulate the operating mechanism, as opposed to accomplishing the procedure itself. The control mechanism, therefore, manipulates the instrument from an initial or neutral position into a ready position for performing the surgical procedure.

For example, the firing system 130, the cartridge assembly 50, and jaws 42, 46 of the instrument 10 constitute an operating mechanism which is designed to staple and divide tissue, as is discussed in detail above. The jaws 42, 46 must be closed before the tissue can be properly stapled and divided, and the jaw closure system 89 is used to control the jaws 42, 46, that is, to bring them into the clamped, ready position. As noted above, once the tip 40 is articulated into a desired position by the surgeon, the tip 40 of the instrument preferably is constrained from further articulation during firing of the instrument. Thus, the clamp-up lever 28 and elastic body 15 therein are used to place the instrument in its ready position by immobilizing the articulation slide control 26 and ultimately the tip 40 at the same time that jaws 42, 46 are closed.

In accordance with preferred aspects of the invention, the instrument 10 includes a passive lockout system and an active lockout system. The passive lockout system immobilizes the firing system 130 when the jaws 42, 46 are in their open position, and when the tip 40 is free to articulate, but allows operation of the firing system 130 when the jaws 42, 46 are closed. The active lockout system immobilizes the firing system 130 until it is manually released by a surgeon. Together, the active and passive lockout systems reduce the risk that instrument 10 will be fired when the jaws 42, 46 are not properly closed or positioned.

In accordance with this aspect of the subject invention, the passive lockout assembly includes a key operatively connected to the control mechanism for reciprocating movement between first and second positions. The first position of the key corresponds to the neutral position of the instrument, and in the first position the key immobilizes the operating mechanism, thereby preventing the instrument from performing the surgical procedure. The second position corresponds to the ready position of the instrument. The key, when it is in its second position releases the operating mechanism, thereby allowing the operating mechanism to perform the surgical procedure.

Instrument 10, in accordance with preferred aspects of the invention, comprises a passive lockout system which includes a pivoting key 152 shown in FIG. 8 which interacts with the clamp-up lever 28 and the link 150. As noted above, clamp-up lever 28 actuates the jaw closure system 89 and closes jaws 42, 46. It also immobilizes the tip 40 of the instrument when it is in its lowered position. As discussed above, link 150 serves to couple the clamp-up lever 28 to the handle 20 so that pivoting of the clamp-up lever 28 from its raised, open position to its lowered, closed position moves the clamp-up driver 90 distally. Clamp-up lever 28, however, through link 150 passively actuates key 152 such that key 152 immobilizes the firing system 130 unless the jaws 42, 46 are closed and the tip 40 is immobilized.

More particularly, as best seen in FIGS. 33–36, link 150 is a generally V-shaped member having a distal arm and a pair of opposed proximal arms extending therefrom. The proximal arms of link 150 have arcuate slots 157 near their ends. Link 150 is pivotally coupled to both the handle 20 and the clamp-up lever 28 via pins 151 as described above.

Pivoting key 152 is a generally L-shaped member having a proximal arm and a distal arm 154. The proximal arm of pivoting key 152 is pivotally coupled near its end to the handle 20 by posts 153 which extend into suitably configured blind bores in handle halves 25, 27. Key 152 also has a pair of posts 158 located near the intersection of its proximal and distal 154 arms which extend through slots 157 in link 150, thereby pivotally coupling key 152 to link 150.

Figure 34:
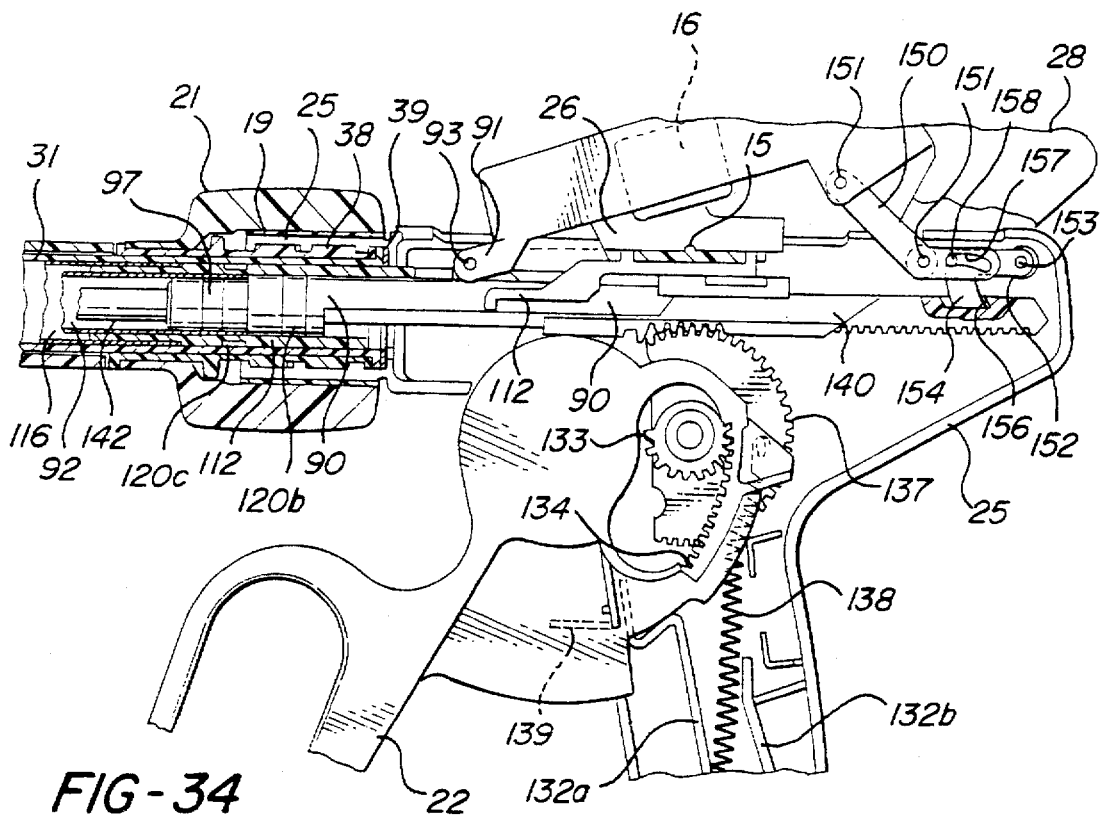
FIGS. 33–36 are a left side elevational views of the handle 20 of instrument 10, certain components thereof being removed, partially torn away, or cross-sectioned along line 33—33 of FIG. 6, showing in particular the passive lockout system, the trigger springs 132, 138, and various drive members in the handle 20 and shaft 30 assemblies.
Figure 33:
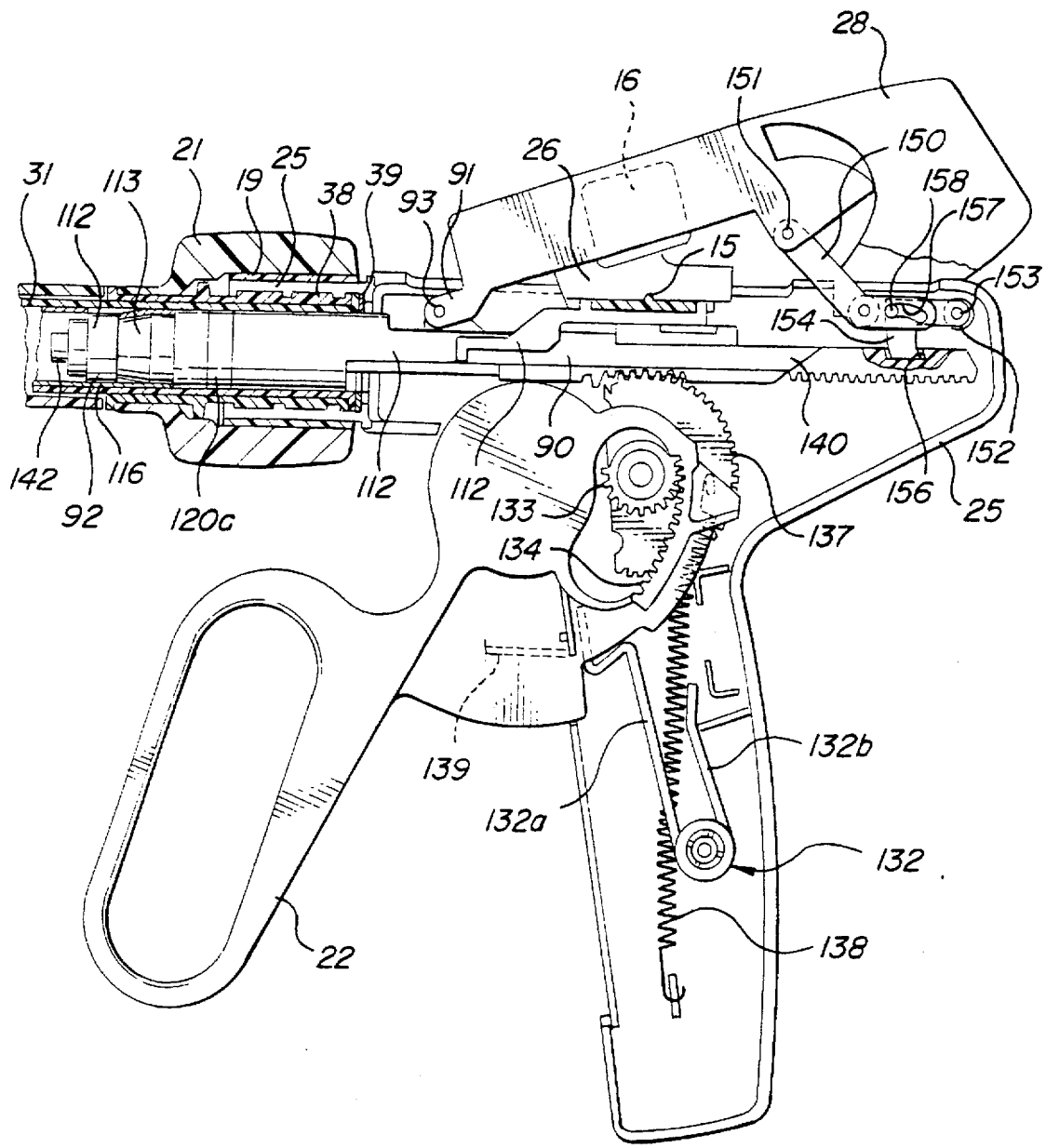

Consequently, when the clamp-up lever is in its raised position (the open-jaw position), link 150 locates key 152 in a lower position as shown in FIGS. 33–34. When key 152 is in its lower position, its distal arm 154 extends downward and engages a notch 156 formed in the upper surface of firing rack 140. Thus, rack 140 cannot move distally, and the instrument 10 cannot be fired when jaws 42, 46 are open and when tip 40 is free to articulate.

Figure 35:
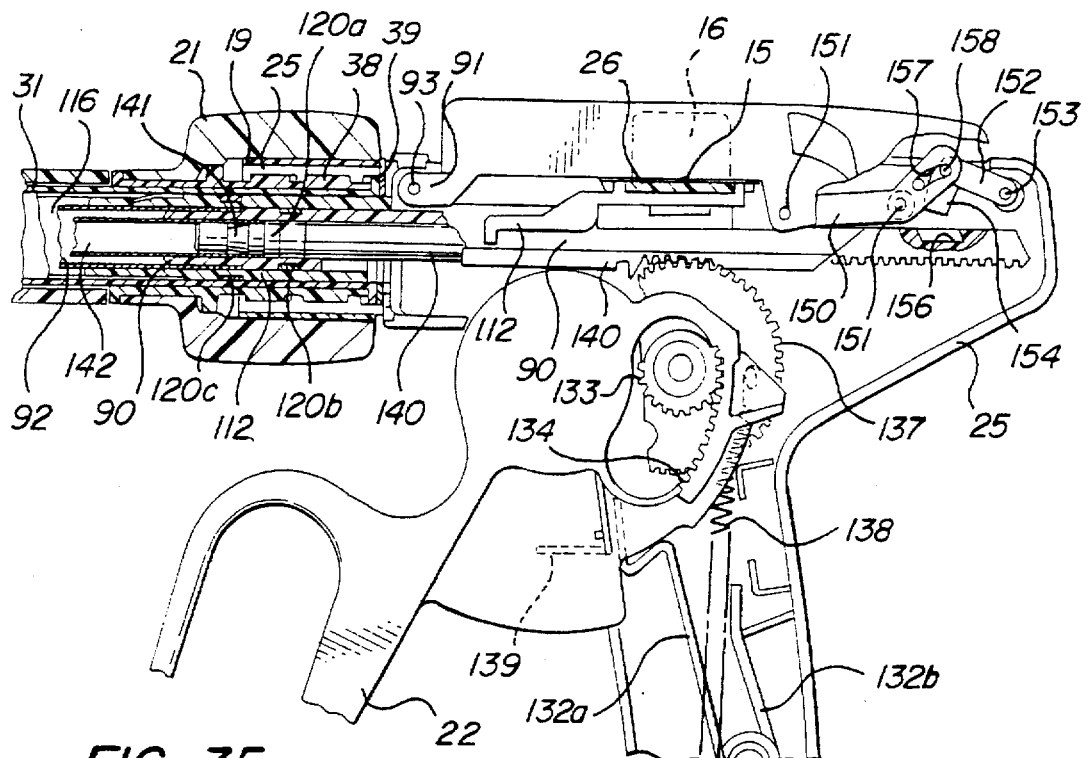
Figure 36:
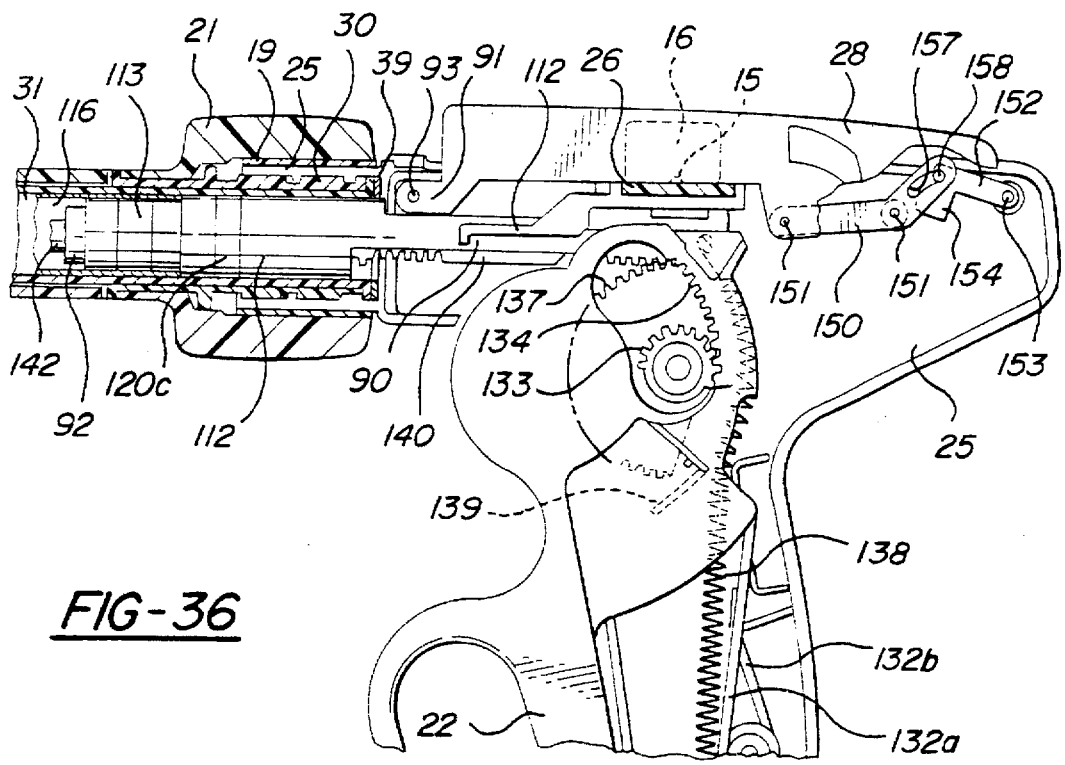

When jaws 42, 46 are closed and the tip 40 is immobilized by moving clamp-up lever from its raised to its lowered position (the closed-jaw position), link 150 causes key 152 to pivot upward as shown in FIG. 35. As key 152 pivots upward, the distal arm 154 likewise pivots out of engagement with rack notch 156. Thus, key 152 no longer prevents rack 140 from moving distally and the instrument 10 from being fired (see FIGS. 35–36) as described in detail above. It will be appreciated, however, that by virtue of slots 157 pivoting of key 152 is delayed somewhat relative to pivoting of clamp-up lever 28 and link 150. The proximal edge of the distal arm 154 of key 152 also is arcuate shaped. Together, the delayed pivoting of key 152 and the arcuate edge of its distal arm 154 ensures that the distal arm 154 of key 152 will remain engaged with rack notch 156 until near the end of the stroke and until the jaws 42, 46 are fully closed and the tip 40 is immobilized.

The passive lockout mechanism described above is preferred in that it reliably locks the firing system unless and until the surgeon clamps the jaws shut. Further, by coordinating the length of the link and key arms, the length and arc of the slot by which the link and key are coupled, and the curve in the edge of the key's distal arm, the timing of release can be easily controlled. The key may be fabricated from plastics by injection molding, and it operates in a manner which takes full advantage of components already commonly employed in the design of linear staplers, a pivoting clamp-up lever and a firing system drive shaft. Thus, it contributes to an instrument which is economically designed and assembled.

Other passive lockout assemblies, however, may be constructed in accordance with the subject invention. For example, the key could be designed to interfere with a boss extending from the firing rack instead of moving in and out of a notch. The key also could be an integral part of the link which couples the clamp-up lever to the handle. In its broadest aspects the subject invention also encompasses keys which translate instead of pivoting and which may engage other components of the firing mechanism instead of a firing rack. Likewise, the novel passive lockout systems may be adapted for use in other instruments, for example, in a clip applier which incorporates separate clip loading and forming mechanisms.

Further in accordance with this aspect of the subject invention, the active lockout system includes a plunger operatively connected to a manually operable switch for reciprocating movement between a first position and a second position. In its first position the plunger immobilizes the operating mechanism, thereby preventing the instrument from performing the surgical procedure. When the plunger is in its second position it releases the operating mechanism. The plunger can be moved from its first position to its second position by manual operation of the switch. It is biased towards its first position, however, such that the plunger returns to its first position after the operating mechanism is actuated.

Accordingly, each time the instrument is used to perform the surgical operation the instrument must be in the ready position and the active lockout switch must be operated. Otherwise, the operating mechanism of the instrument is immobilized by one or both of the passive and active lockout systems.

Figure 37:
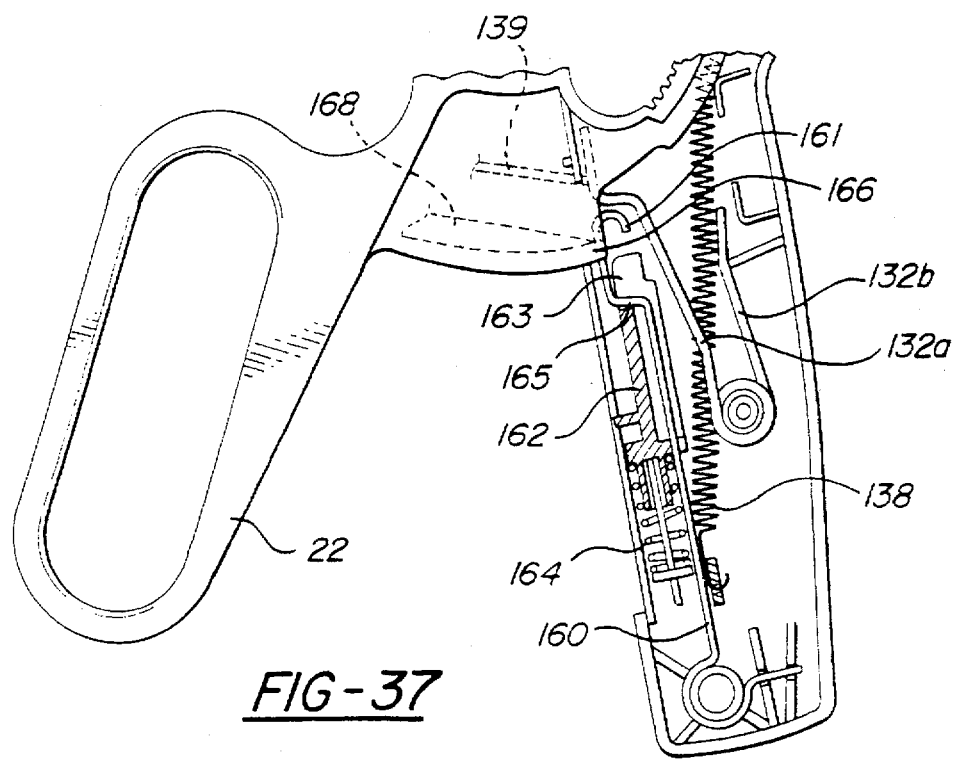
FIG. 37 is a left side elevational, partial view of the handle assembly 20 of instrument 10, certain components thereof being removed or cross-sectioned as in FIG. 33–36, showing in particular the active lockout system.

Instrument 10, in accordance with preferred aspects of the invention, comprises an active lockout system which includes the safety switch 24 previously noted, a plunger 162, a compression spring 164, and a latch 160 shown in FIG. 8 which interact with the trigger 22. The switch 24 is slidably mounted on the exterior distal side of the grip of handle 20 so that it can be easily manipulated by a surgeon, as best seen in FIGS. 1–3. Preferably, bosses 23 are provided on each side of the switch 24 to facilitate manipulation of the switch 24 by the thumb (either left or right) of a surgeon. The switch 24, as shown in FIG. 37, is coupled to plunger 162 which is slidably mounted within an appropriate track 169 (see FIG. 8A) formed on the inside of handle 20. Compression spring 164 biases plunger 162 and switch 24 towards a raised, normal position.

Figures 38, 39:
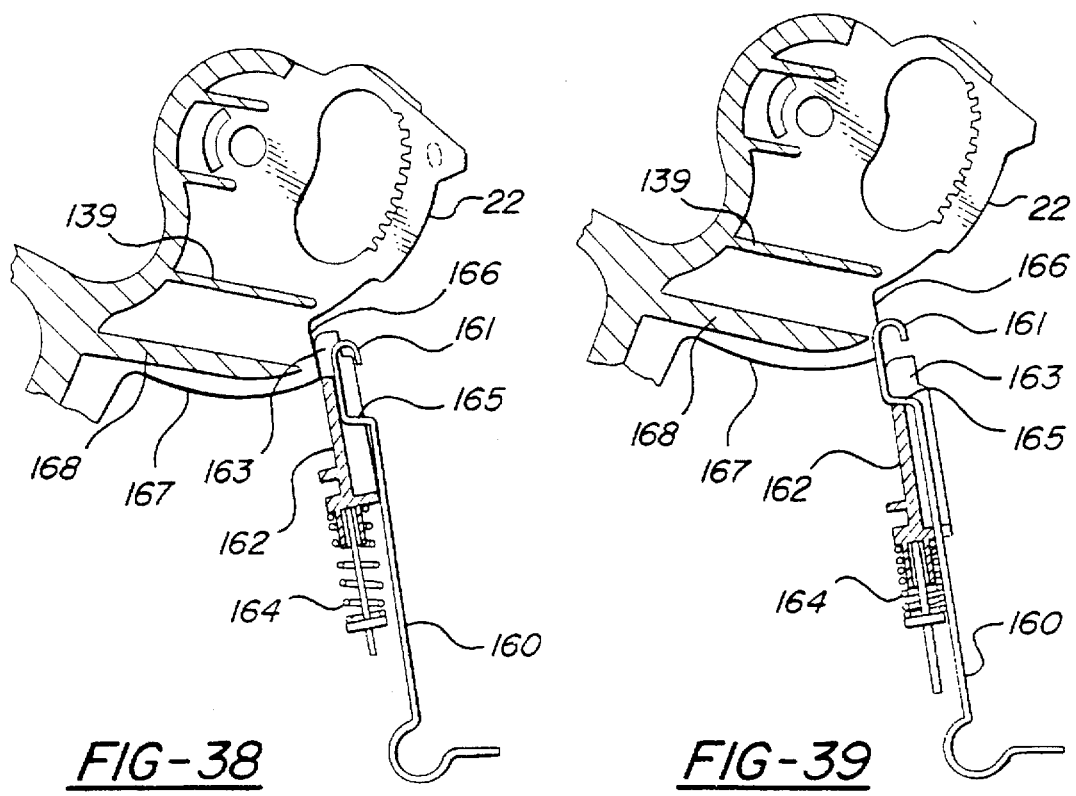
FIGS. 38–42 are cross-sectional views taken generally along line 33—33 of FIG. 6 of the active lockout assembly and trigger in handle assembly 20 of instrument 10 showing those components in various positions.

In its normal, activated position, the upper end of plunger 162 extends into notch 166 formed in the arcuate bottom surface 167 of trigger 22 as shown in FIG. 38. Plunger 162 thereby prevents trigger 22 from pivoting and the instrument 10 from being fired. That is, if the trigger 22 is urged toward the handle 20, the rear surface of notch 166 will abut the forward surface of the upper end of plunger 162.

Latch 160, as shown in FIG. 37, has a fixed arm restrained near the bottom of handle 20. Its free arm extends upwards and terminates in a hook-shaped tip 161 which is offset from the rest of the free arm by a transverse section 165. The latch 160 is preloaded such that its free arm is biased in the distal direction.

When plunger 162 is in its raised, normal position shown in FIG. 38 (compare switch 24 in FIG. 1), latch tip 161 bears on the back surface of plunger 162, the upper end of which plunger 162 as noted engages trigger notch 166. When the switch 24 is slid downward by a surgeon, plunger 162 likewise moves downward and out of engagement with trigger notch 166. At this point, as shown in FIG. 37 and 39, the latch tip 161 passes through a vertical slot 163 formed in the end of plunger 162. The latch tip 161 in this position extends into trigger notch 166 and bears on a contact rib 168 in trigger 22 which terminates at notch 166.

When the switch 24 is released, the bottom surface of plunger slot 163 bears against the transverse section 165 of the free arm of latch 160. Latch 160 thereby engages plunger 162 and holds it in a lowered, disengaged position where it does not block trigger 22 from pivoting (compare switch 24 in FIG. 2). Assuming that the jaws 42, 46 have been clamped shut to disengage the passive lockout system described above, the trigger 22 now can be actuated to fire the instrument 10.

Figure 40:
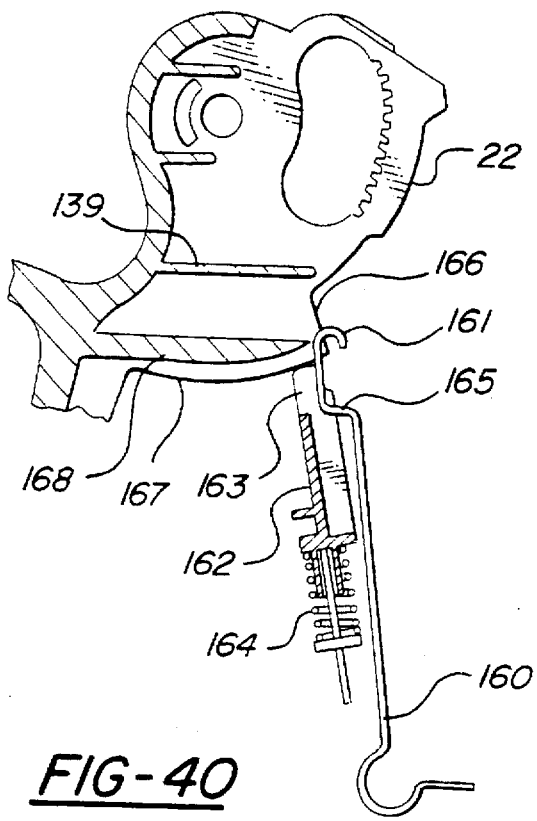
Figure 41:
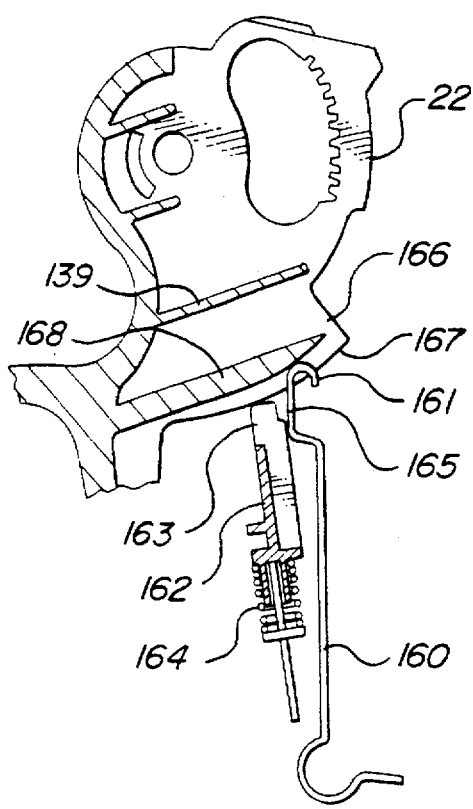

As trigger 22 pivots in firing the instrument 10, the contact rib 168 provides a camming surface which bends latch tip 161 back out of the slot 163 in the end of plunger 162 as shown in FIGS. 40–41. The plunger 162, therefore, is no longer restrained by latch tip 161 and is free to move upwards. Since trigger notch 166 has pivoted out of alignment with the plunger 162, however, plunger 162 shifts slightly upward to an intermediate position in which its top surface bears on the arcuate lower edges 167 of trigger 22 (compare switch 24 in FIG. 3).

Figure 42:
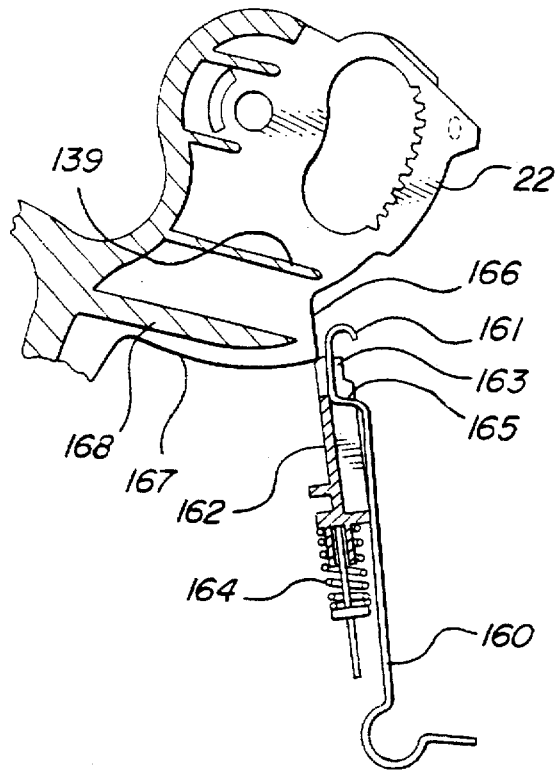

When plunger 162 is in its intermediate position, the slot 163 in its end is no longer aligned with the latch tip 161. Consequently, when the instrument has been fired and trigger 22 pivots back to Has starting position, latch tip 161 ultimately again comes to rest against the back of plunger 162, as shown in FIG. 42, instead of passing back through the slot 163. Plunger 162, therefore, is free to move back to its normal, raised position in which it engages trigger notch 166, as shown in FIG. 38, and trigger 22 is immobilized until switch 24 is manually actuated again.

It will be appreciated, therefore, that the active lockout systems of the subject invention automatically reset after each actuation of the firing trigger. There is no need for a surgeon to manually reset the trigger safety. Thus, the risk that the instrument will be inadvertently fired is reduced.

The active lockout mechanism described above is preferred in that it provides reliable operation and is easily fabricated and assembled. It is readily susceptible to variation to accomplish specific ergonomic characteristics. Further, like the preferred passive lockout systems, the illustrated active lockout system takes advantage of features already commonly employed and preferred in the design of linear staplers, a pistol-type handle with a pivoting trigger. Thus, it contributes to an instrument which is economically designed and assembled.

The novel active lockout systems, however, are subject to considerable variation within the scope of the invention. For example, the latch could be a translating member which relies on a separate resilient member to bias it towards the plunger. The trigger preferably is of the pivoting type, but the novel active lockout systems also can be adapted to translating actuators.

Moreover, the illustrated combination of lockout systems are greatly preferred because, though relatively simple in design, they significantly reduce the likelihood that a surgeon will fire a cartridge before the jaws are properly positioned and clamped over tissue. It will be appreciated, however, that the subject invention encompasses instruments having only an active or a passive lockout system as described herein and instruments in which the novel active lockout systems or the novel passive lockout systems are combined with conventional or other types of safety mechanisms. For example, linear staplers which simply incorporate the passive lockout system or which utilize different active systems may be constructed. Also, since it may nor be necessary to manipulate or lock such instruments in a ready position, the active lockout systems described herein may be used to advantage in clip appliers, cutters and the like.

It will be appreciated from the foregoing that the novel instruments incorporate lockout systems which offer significant performance advantages. Importantly, however, the lockout systems provide such advantages while utilizing a relatively simple design with a minimum number of parts. This simplicity of design facilitates assembly of the instrument, and it allows other mechanical systems to be incorporated into the instrument more easily.

In general, the components of the novel instruments may be fabricated from conventional materials by methods well known to workers in the art. For example, the outer tube 31 of the shaft assembly 30 preferably is constructed of aluminum. The jaws 42, 46 may be fabricated from steel. Parts such as the firing rod 144 and camming driver 94 which are subject to relatively high stress per unit area preferably are fabricated from higher strength materials such as steel. Parts may be fabricated from steel to produce thinner or smaller parts, and so, the firing tube 142, the clamp-up tube 92, and articulation tube 116 preferably are fabricated from thin-walled steel tubing. Other parts which are subject to low stress or which distribute high stresses over a larger area may be fabricated from structural plastics. For example, space constraints are not as great in the handle as they are in the shaft, and thus, the firing rack 140, the clamp-up driver 90, and the articulation driver 112 preferably are fabricated from plastics and have thicker cross-sections. Exterior parts, such as the handle 20 and rotation knob 21, for aesthetic reasons preferably have a smooth, shiny finish, and thus preferably are molded from polycarbonates. Interior plastic components, where aesthetics are less of a concern and mechanical properties are more important, in general may be fabricated from polyamides such as nylon. A variety of structural plastics are known and may be used in fabricating components of the novel instruments.

As will be readily appreciated by those working in the art, the various components of the novel instruments may be provided with a wide variety of bosses/recesses, pins/ openings, and other types of mating or complimentary surface features which facilitate assembly or discourage misassembly of the instrument. In general, however, to simplify the illustration and explication of the preferred embodiment such aspects in general are not shown in the drawings, nor are they always discussed specifically.

In use, a surgeon first inserts the closed jaws 42, 46 and the shaft 30 of the illustrated linear stapler 10 through a cannula. After opening the jaws 42, 46, the surgeon manipulates the articulation slide control 26 and the rotation knob 21 to position the open jaws 42, 46 about the tissue to be stapled and cut. The surgeon then pivots the clamp-up lever 28 downward to clamp the jaws 42, 46 around the tissue. Once the jaws 42, 46 are clamped over the appropriate tissue, the passive lockout system is disengaged, but the active lockout system remains engaged and the instrument 10 still cannot be fired. Consequently, the surgeon actuates the safety switch 24 to activate the instrument 10. At that point the surgeon squeezes the trigger 22 to staple and cut the clamped tissue. The safety switch 24 automatically reactivates. The surgeon then unclamps the tissue, closes the jaws 42, 46, straightens the tip 40, and withdraws the instrument 10 from the cannula. If necessary, the surgeon replaces the spent cartridge 50 with a new one, and repeats the procedure.

Although the invention has been described in connection with certain embodiments, it will be understood that there is no intent to in any way limit the invention to those embodiments. On the contrary, the intent is to cover all alternatives, modifications and equivalents included within the spirit and scope of the invention as defined by the appended claims.

We claim:

1. A surgical instrument including an operating mechanism for repeatedly performing a surgical procedure and a control mechanism for manipulating the instrument between a neutral position and a ready position for performing the surgical procedure, said instrument comprising:

a passive lockout assembly including a key operatively connected to the control mechanism for reciprocating movement between a first position corresponding to the neutral position of said instrument in which said key immobilizes the operating mechanism, thereby preventing said instrument from performing the surgical procedure, and a second position corresponding to the ready position of said instrument in which said key releases the operating mechanism; and an active lockout assembly including a plunger operatively connected to a manually operable switch for reciprocating movement between a first position in which said plunger immobilizes the operating mechanism, thereby preventing the instrument from performing the surgical procedure, and a second position in which said plunger releases the operating mechanism, said plunger being movable to its second position by manual operation of said switch and being biased toward its first position such that said plunger returns to its first position after actuation of the operating mechanism;

whereby each time said instrument is used to perform the surgical operation said instrument must be in the ready position and said active lockout switch must be operated, the operating mechanism of said instrument otherwise being immobilized by one or both of said passive and active lockout assemblies.

2. The surgical instrument of claim 1, wherein said instrument further comprises:

a handle; and an actuator mounted on said handle for reciprocating movement between a first position and a second position, wherein said actuator is operatively connected to the operating mechanism such that movement of said actuator from its first position actuates the operating mechanism and causes it to perform the surgical procedure; and wherein said active lockout assembly further includes a latch mounted in said handle for reciprocating movement between a first position and a second position, wherein said latch is biased toward its first position;

wherein said plunger in is first position engages said actuator in its first position, thereby preventing said actuator from actuating the operating mechanism, and engages said latch, thereby holding said latch in a position intermediate to its first and second positions;

wherein movement of said plunger from its first position to its second position allows said latch to move from its intermediate position to its first position, in which said first position said latch engages said plunger, said latch thereby holding said plunger in its second position and said plunger thereby allowing movement of said actuator from its first position to actuate the operating mechanism;

wherein subsequent movement of said actuator from its first position towards its second position moves said latch from its first position towards its second position, in which said second position said latch is clear of the plunger path, said latch thereby allowing said plunger to move from its second position to an intermediate position in which it is clear of the path of said actuator and interposed in the return path of said latch; and wherein subsequent movement of said actuator back towards its first position allows said plunger to move from its intermediate position back to its first position thereby again preventing said actuator from actuating the operating mechanism;

whereby said switch must be manually operated each time said actuator is returned to its first position.

3. The surgical instrument of claim 1, wherein said instrument further comprises:

a handle; and a trigger mounted on said handle for reciprocating pivoting movement between a first position and a second position, wherein the trigger has a contact surface, a cam surface, and a bearing surface and is operatively connected to the operating mechanism such that pivoting of said trigger actuates the operating mechanism causing it to perform the surgical procedure;

wherein said plunger has first and second bearing surfaces and a contact surface; and wherein said active lockout assembly further includes a resilient member biasing said plunger toward its first position; and a resilient latch mounted in said handle for reciprocating pivoting movement between a first position and a second position, being biased toward its first position, and having a contact surface and a bearing surfaces;

wherein, when said active lockout mechanism is in an activated state, said trigger is in its first position, said plunger is in its first position, and said latch is in a position intermediate its first and second positions such that said trigger contact surface abuts said first plunger bearing surface and said latch contact surface bears on said second plunger bearing surface, said plunger thereby preventing said trigger from actuating the operating mechanism;

wherein said active lockout mechanism is deactivated by operating said switch, thereby moving said plunger from its first position to its second position and allowing said latch to move to its first position;

wherein, when said active lockout mechanism is in its deactivated state, said trigger is in its first position, said plunger is in its second position, and said latch is in its first position such that said first plunger bearing surface is clear of the path of said trigger contact surface, said latch contact surface bears on said trigger cam surface, and said plunger contact surface bears on said latch bearing surface, said latch thereby holding said plunger in its second position and said plunger thereby allowing said trigger to actuate the operating mechanism;

wherein said active lockout mechanism is reactivated by movement of said trigger, movement of said trigger towards its second position thereby moving said latch from its first position towards its second position and allowing said plunger to move to a position intermediate its first and second positions in which said plunger contact surface bears on said trigger bearing surface, said first plunger bearing surface is clear of said trigger contact surface path, and said second plunger bearing surface is interposed in the return path of said latch; and wherein subsequent movement of said trigger back to its first position allows said plunger to return to its first position thereby again preventing said trigger from actuating the operating mechanism.

4. The surgical instrument of claim 1; wherein said instrument further comprises:

a handle; and a trigger mounted on said handle for reciprocating pivoting motion between a first position and a second position, wherein the trigger has an arcuate bearing surface terminating in a notch and is operatively connected to the operating mechanism such that pivoting of said trigger actuates the operating mechanism causing it to perform the surgical procedure; and wherein said active lockout assembly further includes a resilient member biasing said plunger toward its first position; and a resilient latch mounted in said handle for reciprocating pivoting movement between a first position and a second position and being biased toward its first position;

wherein, when said active lockout mechanism is in an activated state, said trigger is in its first position, said plunger is in its first position, and said latch is in a position intermediate its first and second positions such that a portion of said plunger is disposed in said trigger notch, thereby preventing said trigger from actuating the operating mechanism, and said plunger engages said latch, thereby holding said latch in said intermediate position;

wherein said active lockout mechanism is deactivated by operating said switch, thereby moving said plunger from its first position to its second position and allowing said latch to move to its first position;

wherein when said active lockout mechanism is in its deactivated state, said trigger is in its first position, said plunger is in its second position, and said latch is in its first position such that said latch engages said plunger, thereby holding said plunger in its second position, said plunger is clear of said trigger notch, said plunger thereby allowing said trigger to actuate the operating mechanism, and at least a portion of said latch is disposed in said trigger notch;

wherein said active lockout mechanism is reactivated by movement of said trigger, movement of said trigger from its first position towards its second position thereby moving said latch from its first position towards its second position and allowing said plunger to move to a position intermediate its first and second positions in which said plunger bears on said trigger bearing surface; and wherein subsequent movement of said trigger back towards its first position allows said plunger to return to its first position thereby again preventing said trigger from actuating the operating mechanism.

5. The surgical instrument of claim 4, wherein said plunger has a slot extending in an upper end thereof, such that when said active lockout mechanism is in its activated state, said upper end of said plunger is disposed in said trigger notch and said plunger engages said latch at a point below said slot, and when said active lockout mechanism is in its deactivated state, said latch is disposed in said plunger slot and thereby engages and holds said plunger such that its upper end is clear of said trigger notch.

6. The surgical instrument of claim 4, wherein said latch is a torsion spring.

7. The surgical instrument of claim 4, wherein said latch has a hook-shaped tip connected to a latch arm by a transverse section, such that when said active lockout mechanism is in its activated state said latch tip bears on said plunger, when said active lockout mechanism is in its deactivated state said latch transverse section engages said plunger, and when said active lockout mechanism is reactivated by movement of said trigger, said trigger notch bears on said latch tip thereby moving said latch towards its second position.

8. The surgical instrument of claim 4, wherein said plunger has a slot extending in an upper end thereof and said latch is a torsion spring having a hook-shaped tip connected to a latch arm by a transverse section, such that when said active lockout mechanism is in its activated state, said upper end of said plunger is disposed in said trigger notch and said plunger engages said latch tip at a point below said slot, and when said active lockout mechanism is in its deactivated state, said latch transverse section engages said plunger slot and thereby holds said plunger such that its upper end is clear of said trigger notch, and when said active lockout mechanism is reactivated by movement of said trigger, said trigger notch bears on said latch tip thereby moving said latch towards its second position and disengaging said latch transverse section from said plunger slot and allowing said plunger to move to its intermediate position such that its upper end bears on said trigger arcuate bearing surface and to reengage said trigger notch when said trigger is returned to its first position.

9. The surgical instrument of claim 1, wherein said instrument further comprises:
- a handle; and
- an actuator operatively connected to the control mechanism and mounted on said handle for pivoting motion between a first and a second position, such that movement of the actuator from its first to its second position causes the control mechanism to manipulate the instrument from its neutral to its ready position;
- wherein said actuator is pivotally mounted to said handle by a pivoting link; and
- wherein said key is a pivoting key operatively connected to said link such that said key pivots between its said first and second positions.

10. The surgical instrument of claim 9, whereon said surgical instrument further comprises:
- a drive shaft operatively connected to said operating mechanism and mounted in said handle for reciprocating translational movement between a proximal position and a distal position;
- wherein said key in its first position engages and immobilizes said drive shaft in its first position and said key in its second position releases said drive shaft.

11. The surgical instrument of claim 9, wherein said drive shaft has a notch, said key in its first position being disposed in said notch thereby immobilizing said drive shaft and said key in its second position being clear of said notch thereby releasing said drive shaft.

12. The surgical instrument of claim 9, wherein said instrument further comprises:
- a drive shaft mounted in said handle for reciprocating translational movement between a proximal position and a distal position;
- wherein said actuator is a lever arm;
- wherein said pivoting link has first and second arms, said pivoting link being pivotally mounted to said handle at a central pivot point between said first and second link arms;
- wherein said pivoting key has first and second arms, said pivoting key being pivotally mounted on said handle at a pivot point on said second arm;
- wherein said lever arm is pivotally connected to said first link arm and said second link arm is pivotally connected to said pivoting key at a pivot point between said first and second key arms.

13. A surgical instrument including an operating mechanism for performing a surgical procedure, said instrument comprising:
- a handle;
- an actuator mounted on said handle for reciprocating movement between a first position and second position, wherein said actuator is operatively connected to the operating mechanism such that movement of said actuator from its first position actuates the operating mechanism and causes it to perform the surgical procedure;
- a latch mounted in said handle for reciprocating movement between a first position and a second position, wherein said latch is biased toward its first position;
- a plunger mounted in said handle for reciprocating translational movement between a first position, in which said first position said plunger engages said actuator in its first position, thereby preventing said actuator from actuating the operating mechanism; and engages said latch, thereby holding said latch in a position intermediate to its first and second positions, and a second position in which said plunger disengages said actuator, said plunger being biased toward its first position;
- a manually operated switch operably connected to said plunger such that operation of said switch moves said plunger from its first to its second position;
- wherein movement of said plunger from its first position to its second position allows said latch to move from its intermediate position to its first position, in which said first position said latch engages said plunger, said latch thereby holding said plunger in its second position and said plunger thereby allowing movement of said actuator from its first position to actuate the operating mechanism;

wherein subsequent movement of said actuator from its first position towards its second position moves said latch from its first position towards its second position in which said second position said latch is clear of the plunger path, said latch thereby allowing said plunger to move from its second position to an intermediate position in which it is clear of the path of said actuator and interposed in the return path of said latch; and wherein subsequent movement of said actuator back towards its first position allows said plunger to move from its intermediate position back to its first position thereby again preventing said actuator from actuating the operating mechanism;

whereby said switch must be manually operated each time said actuator is returned to its first position.

14. A surgical instrument including an operating mechanism for performing a surgical procedure, said instrument comprising:

a handle;

a trigger mounted on said handle for reciprocating pivoting movement between a first position and a second position, wherein the trigger has a contact surface, a cam surface, and a bearing surface and is operatively connected to the operating mechanism such that pivoting of said trigger actuates the operating mechanism causing it to perform the surgical procedure;

an active lockout assembly having an activated and a deactivated state and including a plunger mounted in said handle for reciprocating translational movement between a first position and a second position and having first and second bearing surfaces and a contact surface;

a manually operable switch operatively connected to said plunger;

a resilient member biasing said plunger toward its first position;

a resilient latch mounted in said handle for reciprocating pivoting movement between a first position and a second position, being biased toward its first position, and having a contact surface and a bearing surface;

wherein, when said active lockout mechanism is in its activated state, said trigger is in its first position, said plunger is in its first position, and said latch is in a position intermediate its first and second positions such that said trigger contact surface abuts said first plunger bearing surface and said latch contact surface bears on said second plunger bearing surface, said plunger thereby preventing said trigger from actuating the operating mechanism;

wherein said active lockout mechanism is deactivated by operating said switch, thereby moving said plunger from its first position to its second position and allowing said latch to move to its first position;

wherein, when said active lockout mechanism is in its deactivated state, said trigger is in its first position, said plunger is in its second position, and said latch is in its first position such that said first plunger bearing surface is clear of the path of said trigger contact surface, said latch contact surface bears on said trigger cam surface, and said plunger contact surface bears on said latch bearing surface, said latch thereby holding said plunger in its second position and said plunger thereby allowing said trigger to actuate the operating mechanism;

wherein said active lockout mechanism is reactivated by movement of said trigger, movement of said trigger towards its second position thereby moving said latch from its first position towards its second position and allowing said plunger to move to a position intermediate its first and second positions in which said plunger contact surface bears on said trigger bearing surface, said first plunger bearing surface is clear of said trigger contact surface paths, and said second plunger bearing surface is interposed in the return path of said latch; and wherein subsequent movement of said trigger back to its first position allows said plunger to return to its first position thereby again preventing said trigger from actuating the operating mechanism.

15. In a surgical instrument including an operating mechanism for repeatedly performing a surgical procedure, a control mechanism for manipulating the instrument between a neutral position and a ready position for performing the surgical procedure, a passive safety mechanism preventing the instrument from performing the surgical procedure unless the instrument is in its ready position, and an active safety mechanism preventing the instrument from performing the surgical procedure unless the active safety mechanism is deactivated, the improvement comprising:

a passive lockout assembly including a key operatively connected to the control mechanism for reciprocating movement between a first position corresponding to the neutral position of the instrument in which said key immobilizes the operating mechanism, thereby preventing the instrument from performing the surgical procedure, and a second position corresponding to the ready position of the instrument in which said key releases the operating mechanism; and an active lockout assembly including a plunger operatively connected to a manually operable switch for reciprocating movement between a first position in which said plunger immobilizes the operating mechanism, thereby preventing the instrument from performing the surgical procedure, and a second position in which said plunger releases the operating mechanism, said plunger being movable to its second position by manual operation of said switch and being biased toward its first position such that said plunger returns to its first position after actuation of the operating mechanism;

whereby each time the instrument is used to perform the surgical operation the instrument must be in the ready position and said active lockout switch must be operated, the operating mechanism of the instrument otherwise being immobilized by one or both of said passive and active lockout assemblies.

16. In a surgical instrument including an operating mechanism for performing a surgical procedure; a handle; an actuator mounted on the handle for reciprocating movement between a first position and a second position, wherein the actuator is operatively connected to the operating mechanism such that movement of the actuator from its first position actuates the operating mechanism and causes it to perform the surgical procedure, and an active safety mechanism preventing the instrument from performing the surgical procedure unless the active safety mechanism is deactivated; the improvement comprising:

a latch mounted in the handle for reciprocating movement between a first position and a second position, wherein said latch is biased toward its first position;

a plunger mounted in the handle for reciprocating translational movement between a first position, in which said first position said plunger engages the actuator in its first position, thereby preventing the actuator from actuating the operating mechanism, and engages said latch, thereby holding said latch in a position intermediate to its first and second positions, and a second position in which said plunger disengages the actuator, said plunger being biased toward its first position;

a manually operated switch operably connected to said plunger such that operation of said switch moves said plunger from its first to its second position;

wherein movement of said plunger from its first position to its second position allows said latch to move from its intermediate position to its first position, in which said first position said latch engages said plunger, said latch thereby holding said plunger in its second position and said plunger thereby allowing movement of the actuator from its first position to actuate the operating mechanism;

wherein subsequent movement of the actuator from its first position towards its second position moves said latch from its first position towards its second position, in which said second position said latch is clear of the plunger path, said latch thereby allowing said plunger to move from its second position to an intermediate position in which it is clear of the path of the actuator and interposed in the return path of said latch; and wherein subsequent movement of the actuator back towards its first position allows said plunger to move from its intermediate position back to its first position thereby again preventing the actuator from actuating the operating mechanism;

whereby said switch must be manually operated each time the actuator is returned to its first position.

* * * * *